(12) United States Patent  
Samade et al.

(10) Patent No.: US 8,798,740 B2  
(45) Date of Patent: Aug. 5, 2014

(54) SINGLE CHAMBER LEADLESS INTRA-CARDIAC MEDICAL DEVICE WITH DUAL-CHAMBER FUNCTIONALITY

(75) Inventors: Richard Samade, Northridge, CA (US); Edward Karst, South Pasadena, CA (US); Gene A. Bornzin, Simi Valley, CA (US); John W. Poore, South Pasadena, CA (US); Zoltan Somogyi, Simi Valley, CA (US); Didier Theret, Porter Ranch, CA (US); Nirav Dalal, Porter Ranch, CA (US)

(73) Assignee: PaceSetter, Inc., Sylmar, CA (US)

( * ) Notice: Subject to any disclaimer, the term of this patent is extended or adjusted under 35 U.S.C. 154(b) by 0 days.

(21) Appl. No.: 13/352,048

(22) Filed: Jan. 17, 2012

(65) Prior Publication Data

US 2013/0116738 A1 May 9, 2013

Related U.S. Application Data

(60) Provisional application No. 61/555,386, filed on Nov. 3, 2011.

(51) Int. Cl.  
*A61N 1/00* (2006.01)

(52) U.S. Cl.  
USPC ........ 607/4; 607/9; 607/30; 607/33; 607/126; 607/127; 607/128; 607/129; 607/130

(58) Field of Classification Search  
CPC ......... A61N 1/3605; A61N 1/36; A61N 1/32; A61N 1/3756; A61N 1/3684; A61N 1/0573; A61M 5/1723  
USPC .............................. 607/4, 9, 30, 33, 126–130  
See application file for complete search history.

(56) References Cited

U.S. PATENT DOCUMENTS

| | | | |
|---|---|---|---|
| 2006/0136004 A1* | 6/2006 | Cowan et al. | 607/33 |
| 2008/0082132 A1* | 4/2008 | Annest et al. | 607/4 |
| 2010/0069983 A1* | 3/2010 | Peacock et al. | 607/9 |

* cited by examiner

*Primary Examiner* — Niketa Patel  
*Assistant Examiner* — Lindsey G Hankins

(57) ABSTRACT

A leadless intra-cardiac medical device (LIMD) includes a housing configured to be implanted entirely within a single local chamber of the heart.

32 Claims, 17 Drawing Sheets

SINGLE CHAMBER LEADLESS INTRA-CARDIAC MEDICAL DEVICE WITH DUAL-CHAMBER FUNCTIONALITY

CROSS REFERENCE TO RELATED APPLICATIONS

This application relates to and claims priority benefits from U.S. Provisional Application No. 61/555,386, filed Nov. 3, 2011, entitled "Single Chamber Leadless Implantable Medical Device with Dual Chamber Functionality," which is hereby incorporated by reference in its entirety. This application also relates to U.S. patent application Ser. No.: 13/352,101, filed Jan. 17, 2012, entitled "Single-Chamber Leadless Intra-Cardiac Medical Device with Dual Chamber Functionality and Shaped Stabilization Intra-Cardiac Extension", and U.S. patent application Ser. No. 13/352,136, filed Jan. 17, 2012, entitled "Dual-Chamber Leadless Intra-Cardiac Medical Device with Intra-Cardiac Extension", which are hereby incorporated by reference in their entirety

FIELD OF THE INVENTION

Embodiments of the present invention generally relate to implantable medical devices, and more particularly to leadless intra-cardiac medical devices that afford dual chamber functionality from a position within a single chamber of the heart. As used herein, the term "leadless" generally refers to an absence of electrically-conductive leads that traverse vessels or other anatomy outside of the intra-cardiac space, while "intra-cardiac" means generally, entirely within the heart and associated vessels, such as the SVC, IVC, CS, pulmonary arteries and the like.

BACKGROUND OF THE INVENTION

Current implantable medical devices (IMD) for cardiac applications, such as pacemakers, include a "housing" or "can" and one or more electrically-conductive leads that connect to the can through an electro-mechanical connection. The can is implanted outside of the heart, in the pectoral region of a patient and contains electronics (e.g., a power source, microprocessor, capacitors, etc.) that provide pacemaker functionality. The leads traverse blood vessels between the can and heart chambers in order to position one or more electrodes carried by the leads within the heart, thereby allowing the device electronics to electrically excite or pace cardiac tissue and measure or sense myocardial electrical activity.

To sense atrial cardiac signals and to provide right atrial chamber stimulation therapy, the can is coupled to an implantable right atrial lead including at least one atrial tip electrode that typically is implanted in the patient's right atrial appendage. The right atrial lead may also include an atrial ring electrode to allow bipolar stimulation or sensing in combination with the atrial tip electrode.

Before implantation of the can into a subcutaneous pocket of the patient, however, an external pacing and measuring device known as a pacing system analyzer (PSA) is used to ensure adequate lead placement, maintain basic cardiac functions, and evaluate pacing parameters for an initial programming of the device. In other words, a PSA is a system analyzer that is used to test an implantable device, such as an implantable pacemaker.

To sense the left atrial and left ventricular cardiac signals and to provide left-chamber stimulation therapy, the can is coupled to the "coronary sinus" lead designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead is designed to: receive atrial and/or ventricular cardiac signals; deliver left ventricular pacing therapy using at least one left ventricular tip electrode for unipolar configurations or in combination with left ventricular ring electrode for bipolar configurations; deliver left atrial pacing therapy using at least one left atrial ring electrode as well as shocking therapy using at least one left atrial coil electrode.

To sense right atrial and right ventricular cardiac signals and to provide right-chamber stimulation therapy, the can is coupled to an implantable right ventricular lead including a right ventricular (RV) tip electrode, a right ventricular ring electrode, a right ventricular coil electrode, a superior vena cava (SVC) coil electrode, and so on. Typically, the right ventricular lead is inserted transvenously into the heart so as to place the right ventricular tip electrode in the right ventricular apex such that the RV coil electrode is positioned in the right ventricle and the SVC coil electrode will be positioned in the right atrium and/or superior vena cava. Accordingly, the right ventricular lead is capable of receiving cardiac signals, and delivering stimulation in the form of pacing and shock therapy to the right ventricle.

Although a portion of the leads are located within the heart, a substantial portion of the leads, as well as the can itself are outside of the patient's heart. Consequently, bacteria and the like may be introduced into the patient's heart through the leads, as well as the can, thereby increasing the risk of infection within the heart. Additionally, because the can is outside of the heart, the patient may be susceptible to Twiddler's syndrome, which is a condition caused by the shape and weight of the can itself. Twiddler's syndrome is typically characterized by a subconscious, inadvertent, or deliberate rotation of the can within the subcutaneous pocket formed in the patient. In one example, a lead may retract and begin to wrap around the can. Also, leads may dislodge from the endocardium and cause the device to malfunction. Further, in another typical symptom of Twiddler's syndrome, the device may stimulate the diaphragm, vagus, or phrenic nerve, pectoral muscles, or brachial plexus. Overall, Twiddler's syndrome may result in sudden cardiac arrest due to conduction disturbances related to the device.

In addition to the foregoing complications, implanted leads may experience certain further complications, such as incidences of venous stenosis or thrombosis, device-related endocarditis, lead perforation of the tricuspid valve and concomitant tricuspid stenosis; and lacerations of the right atrium, superior vena cava, and innominate vein or pulmonary embolization of electrode fragments during lead extraction.

To combat the foregoing limitations and complications, small sized devices configured for intra-cardiac implant have been proposed. These devices, termed leadless pacemakers (LLPM), are typically characterized by the following features: they are devoid of leads that pass out of the heart to another component, such as a pacemaker can outside of the heart; they include electrodes that are affixed directly to the can of the device; the entire device is attached to the heart; and the device is capable of pacing and sensing in the chamber of the heart where it is implanted.

LLPM devices that have been proposed thus far offer limited functional capability. These LLPM devices are able to sense in one chamber and deliver pacing pulses in that same chamber, and thus offer single chamber functionality. For example, an LLPM device that is located in the right atrium would be limited to offering AAI mode functionality. An AAI mode LLPM can only sense in the right atrium, pace in the right atrium and inhibit pacing function when an intrinsic event is detected in the right atrium within a preset time limit. Similarly, an LLPM device that is located in the right ventricle would be limited to offering VVI mode functionality. A VVI mode LLPM can only sense in the right ventricle, pace in the right ventricle and inhibit pacing function when an intrinsic event is detected in the right ventricle within a preset time limit. To gain widespread acceptance by clinicians, it would be highly desired for LLPM devices to have dual chamber pacing/sensing capability (DDD mode) along with other features, such as rate adaptive pacing.

It has been proposed to implant sets of multiple LLPM devices within a single patient, such as one or more LLPM devices located in the right atrium and one or more LLPM devices located in the right ventricle. The atrial LLPM devices and the ventricular LLPM devices wirelessly communicate with one another to convey pacing and sensing information there between to coordinate pacing and sensing operations between the various LLPM devices.

However, these sets of multiple LLPM devices experience various limitations. For example, each of the LLPM devices must expend significant power to maintain the wireless communications links. The wireless communications links should be maintained continuously in order to constantly convey pacing and sensing information between, for example, atrial LLPM device(s) and ventricular LLPM device(s). This pacing and sensing information is necessary to maintain continuous synchronous operation, which in turn draws a large amount of battery power.

Further, it is difficult to maintain a reliable wireless communications link between LLPM devices. The LLPM devices utilize low power transceivers that are located in a constantly changing environment within the associated heart chamber. The transmission characteristics of the environment surrounding the LLPM device change due in part to the continuous cyclical motion of the heart and change in blood volume. Hence, the potential exists that the communications link is broken or intermittent.

SUMMARY OF THE INVENTION

In accordance with one embodiment, a leadless intra-cardiac medical device (LIMD) is provided with dual chamber functionality, without leads, despite the fact that the entire device is located in one chamber. In one embodiment, the LIMD stimulates and senses the right atrium (RA) and right ventricle (RV) chambers, even though it is entirely located in the RA. The electrodes enable delivering stimulus and sensing in different chambers of the heart and thus provide physiological synchronization of myocardial contraction in multiple chambers.

In another embodiment, an LIMD is provided that may be located in the RV, deliver stimulus and sense either the RA or the left ventricle (LV). Alternatively, the LIMD may be located in the RA and configured to electrically stimulate the RV and LV. This last LLPM configuration or placement may be done in a manner such that Hisian or para-Hisian pacing is achieved.

In accordance with an embodiment, a leadless intra-cardiac medical device (LIMD) is provided, comprised of a housing configured to be implanted entirely within a single local chamber of the heart, the local chamber having local wall tissue that constitutes part of a conduction network of the local chamber. A base is provided on the housing, the base configured to be secured to a septum that separates the local chamber from an adjacent chamber, the adjacent chamber having distal wall tissue, with respect to the local chamber that constitutes part of a conduction network of the adjacent chamber. A first electrode is provided at a first position on the base such that, when the device is implanted in the local chamber, the first electrode engages wall tissue at a local activation site within the conduction network of the local chamber. A second electrode is provided at a second position on the base and extending outward such that, when the device is implanted in the local chamber, the second electrode engages wall tissue at a distal activation site within the conduction network of the adjacent chamber. A controller is provided within the housing to cause stimulus pulses to be delivered, in a synchronous manner, through the first and second electrodes to the local and distal activation sites, respectively, such that stimulus pulses delivered at the distal activation site are timed to cause contraction of the adjacent chamber in a predetermined relation to contraction of the local chamber. Optionally, the controller is configured to control delivery of the stimulus pulses from the first and second electrodes in accordance with a DDD pacing mode or a DDDR pacing mode.

Optionally, the septum represents a portion of the triangle of Koch and ventricular vestibule. The second electrode is configured to engage the distal activation site which is in the ventricular vestibule. The first electrode is configured to engage the local activation site which is in the triangle of Koch. The first and second electrodes deliver stimulus pulses to the triangle of Koch and the ventricular vestibule to initiate activation in a right atrium and right ventricle, respectively.

Optionally, the controller is configured to control delivery, from the first and second electrodes, of the stimulus pulses to a right atrium and a right ventricle, while the LIMD is entirely located in one of the right atrium and right ventricle.

Optionally, the adjacent chamber constitutes at least one of a left atrium, a right ventricle and a left ventricle, the distal activation site being physiologically responsive to distal activation events originating in the at least one of left atrium, right ventricle and left ventricle. At least one of the first and second electrodes may represent surface bump type electrodes that passively engage the wall tissue. The base may include mounting elements to secure the first and second electrodes to the housing in an electrically isolated manner. The second electrode may have different first and second cross-sections at proximal and distal ends thereof. The second electrode may include a conductive wire that has a different first and second iso-diameters at the proximal and distal ends thereof. The base may include at least one of spikes and a serrated edge to facilitate active fixation to the septum.

In accordance with an embodiment, a method is provided for implanting a leadless intra-cardiac medical device (LIMD), the method comprised of loading a device into an introducer. The device has a base with first and second electrodes provided thereon, guiding the device, utilizing the introducer, to an activation site that is located entirely within a single local chamber of the heart and proximate to a septum. The local chamber has local wall tissue that constitutes part of a conduction network of the local chamber. The septum separates the local chamber from an adjacent chamber. The adjacent chamber has distal wall tissue, with respect to the local chamber that constitutes part of a conduction network of the adjacent chamber. The method includes positioning the first electrode to engage wall tissue at a local activation site within the conduction network of the local chamber, positioning the second electrode to engage wall tissue at a distal activation site within the conduction network of the adjacent chamber, and actively securing the device to the tissue of interest, such as a septum. The method further includes configuring a controller within the housing to cause stimulus pulses to be delivered through the first and second electrodes to the local and distal activation sites, respectively, such that stimulus pulses delivered at the distal activation site are timed to cause contraction of the adjacent chamber in a predetermined relation to contraction of the local chamber.

The introducer has a distal end that is open to permit the device to be deployed there through once the device is actively secured to the septum. The method may further comprise securing a pusher tool to a proximal end of the device within the introducer and utilizing the pusher tool to guide the device into position, and rotate the device to actively secure a fixation member on the base of the device to the tissue of interest. Optionally, the method further comprises performing a capture test to evaluate whether at least one of the first and second electrodes are electrically coupled to at least one of the conduction networks of the local and adjacent chambers.

In accordance with an embodiment, a leadless intra-cardiac medical device (LIMD) is provided, comprised of a housing configured to be implanted entirely within a single local chamber of the heart, the local chamber having local wall tissue that constitutes part of a conduction network of the local chamber. A base is provided on the housing, the base configured to be secured to a septum that separates the local chamber from an adjacent chamber, the adjacent chamber having distal wall tissue, with respect to the local chamber that constitutes part of a conduction network of the adjacent chamber. A first electrode is provided on the base and extending outward such that, when the device is implanted in the local chamber, the first electrode engages wall tissue at a distal activation site within the conduction network of the adjacent chamber. An extension arm is provided on the housing and extending outward from the housing. A second electrode is provided on the extension arm and located such that, when the extension arm is positioned in the local chamber, the second electrode engages wall tissue at a local activation site within the conduction network of the local chamber. A controller is provided within the housing to cause stimulus pulses to be delivered, in a synchronous manner, through the first and second electrodes to the distal and local activation sites, respectively, such that stimulus pulses delivered at the distal activation site are timed to cause contraction of the adjacent chamber in a predetermined relation to contraction of the local chamber.

The housing further comprises a stabilizer arm having a distal end that extends outward from the housing, the stabilizer arm having a pusher cup located at the distal end, the stabilizer arm having a core structure that is torque and compression resistant such that when the pusher tool is rotated or moved longitudinally, the stabilizer arm conveys rotation and longitudinal force from the pusher tool to the housing.

The housing further comprises a stabilizer arm joined to a top end of the housing, the extension arm having the second electrode located on a distal end thereof to extend into and engage the local wall tissue in an appendage area of the local chamber, the stabilizer arm having a distal end that extends to and engages an opposed stabilization area of the local chamber. The housing further comprises a stabilizer arm, the extension arm and stabilizer arm pivotally joined to a hinge assembly located at a top end of the housing.

The housing further comprises a stabilizer arm, the extension arm and stabilizer arm securely joined to a top end of the housing, the extension arm and stabilizer arm being biased to flare outward away from one another when in a deployed position such that distal ends of the stabilization and extension arms engage the local chamber in opposed areas remote from the base of the housing.

Optionally, the housing is elongated along a longitudinal axis, the housing being joined to the extension arm such that the extension arm moves between an introduction contracted position substantially in-line with the longitudinal axis of the housing and a deployed flared position that projects at an acute angle from the longitudinal axis of the housing to position the first electrode against the local wall tissue.

In accordance with an embodiment, a method is provided for implanting a leadless intra-cardiac medical device (LIMD), the method comprises loading a device into an introducer, the device having a housing with a base and with an extension arm, the extension arm extending outward from the housing, the device having a first electrode provided on the base and a second electrode provided on the extension arm. The method including guiding the device, utilizing the introducer, to an activation site that is located entirely within a single local chamber of the heart and proximate to a septum, the local chamber having local wall tissue that constitutes part of a conduction network of the local chamber, the septum separating the local chamber from an adjacent chamber, the adjacent chamber having distal wall tissue, with respect to the local chamber, that constitutes part of a conduction network of the adjacent chamber. The method further includes actively securing the device to tissue of interest, such as a septum and positions the first electrode to engage wall tissue at a distal activation site within the conduction network of the adjacent chamber and positioning the second electrode to engage wall tissue at a local activation site within the conduction network of the local chamber. The method also includes configuring a controller within the housing to cause stimulus pulses to be delivered through the first and second electrodes to the distal and local activation sites, respectively, such that stimulus pulses delivered at the distal activation site are timed to cause contraction of the adjacent chamber in a predetermined relation to contraction of the local chamber.

The method also comprises deploying the extension arm to engage the local wall tissue in an appendage area of the local chamber. The method may also comprise deploying the extension arm to extend into and engage the local wall tissue in an appendage area of the local chamber, and deploying a distal end of a stabilizer arm joined to the housing to extend to and engage an opposed stabilization area of the local chamber. The method may further comprise and extending a stabilizer arm on the housing engage a superior vena cava of the heart. Optionally, the method includes connecting a pusher tool to a distal end of a stabilizer arm of the device, and joining a proximal end of the stabilizer arm to the housing, the stabilizer arm having a core structure that is torque and compression resistant such that when the pusher tool is rotated or moved longitudinally, the stabilizer arm conveys rotation and longitudinal force from the pusher tool to the housing. The method comprises securing a pusher tool to a proximal end within the introducer, utilizing the pusher tool to guide the device into position, and utilizing the pusher tool to rotate the device to actively secure a fixation member on the base of the device to the tissue of interest. Optionally, the method comprises implanting the device such that the first electrode engages the distal activation site which is in the ventricular vestibule and the second electrode engage the local activation site which is in the right atrial appendage.

BRIEF DESCRIPTION OF THE DRAWINGS

FIG. 4A illustrates a LIMD that has a base with spikes extending there from.

DETAILED DESCRIPTION

Figure 1:
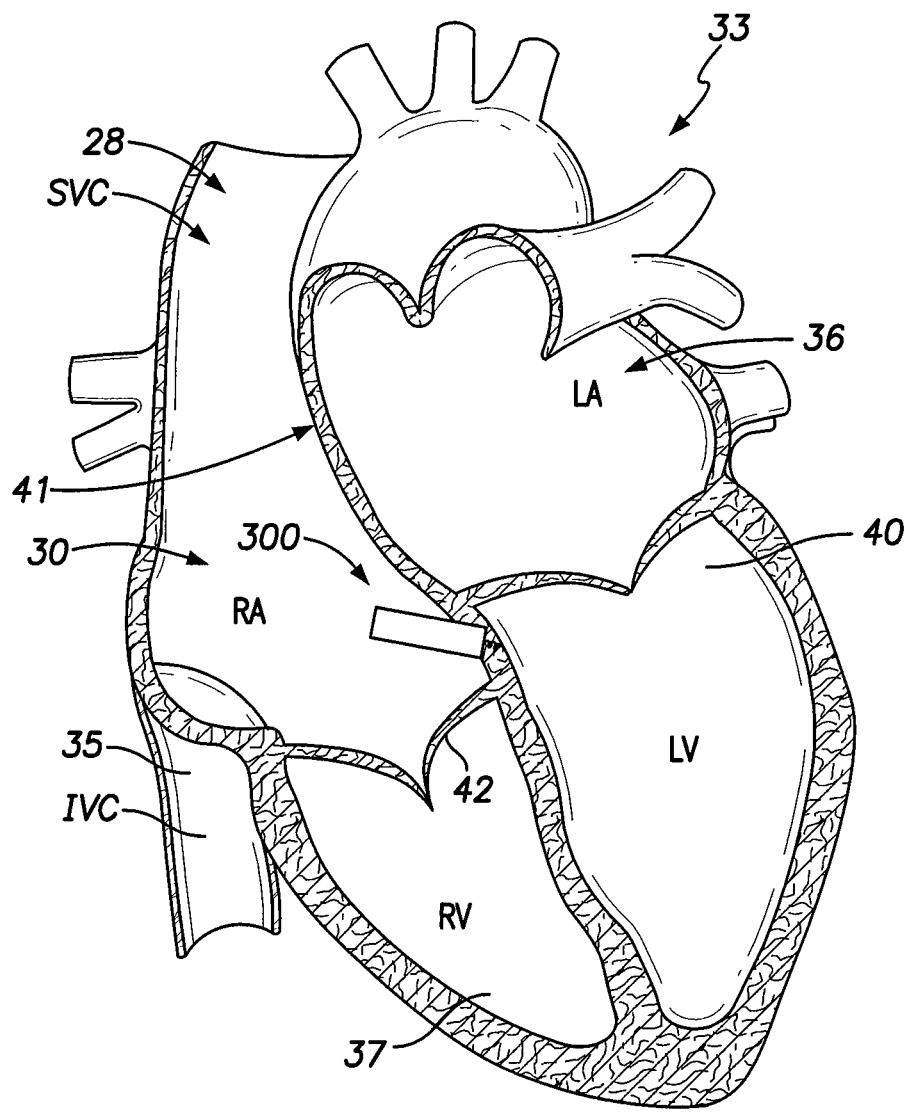
FIG. 1 illustrates a sectional view of a patient's heart with a leadless intra-cardiac medical device (LIMD) implanted therein.

Dual-chamber permanent pacemakers (PPM) operating in the DDD or DDDR mode, are indicated for patients with complete atrioventricular (AV) block, sick sinus syndrome, and paroxysmal AV block. The use of DDD or DDDR mode PPMs in patients with a high degree of AV block is shown to improve subjective metrics of patient life and increase peak velocity and cardiac output, compared to VVIR PPMs. Additionally, another study demonstrates reduced incidence of atrial fibrillation (AF) and increased patient longevity in patients with sick sinus syndrome after the time of DDDR PPM implant. These significant benefits, accrued to the three previously-described subgroups of implant patients, provide a strong impetus for using DDDR PPMs in those recipients.

The benefits of conventional DDD or DDDR PPMs are counterbalanced by the increased risk of complications with the additional lead necessary for these PPMs (compared to single-chamber devices). A preferred solution to this dilemma as offered by embodiments herein eliminate the need to use leads by providing an LIMD with DDDR mode functionality. As a result, patients suffering from various degrees of AV block or sick sinus syndrome may receive dual-chamber pacing therapy without an increased risk of complications (such as lead-associated infections caused by biofilm formation 14 or explant-related difficulties). In particular, decreased incidence of device-related infections may be achieved by a DDDR mode-capable LIMD as a result of the device body's small surface area (compared to conventional PPMs and leads), which presents a reduced substrate for bacterial or fungal adhesion.

Myocardial contraction results from a change in voltage across the cell membrane (depolarization), which leads to an action potential. Although contraction may happen spontaneously, it is normally in response to an electrical impulse. In normal physiologic behavior, this impulse starts in the sino-atrial (SA) node where a collection of cells are located at the junction of the right atrium and superior vena cava. These specialized cells depolarize spontaneously, and cause a wave of contraction to follow a conduction network along the tissue wall of the atria. Following atrium contraction, the impulse is delayed at the atrio-ventricular (AV) node, located in the septum wall of the right atrium. From here HIS-Purkinje fibers allow rapid conduction of the electrical impulse to propagate along the conduction network formed by the right and left branches in the RV and LV tissue walls, causing almost simultaneous depolarization of both ventricles, approximately 0.2 seconds after the initial impulse has arisen in the sino-atrial node. Depolarization of the myocardial cell membrane causes a large increase in the concentration of calcium within the cell, which in turn causes contraction by a temporary binding between two proteins, actin and myosin. The cardiac action potential is much longer than that of skeletal muscle, and during this time the myocardial cell is unresponsive to further excitation. Hence, in a general sense, the tissue walls of each chamber constitute part of a conduction network of the corresponding chamber.

FIG. 1 provides a sectional view of a patient's heart 33 and shows a leadless intra-cardiac medical device 300. The leadless implantable medical device 300 has been placed through the superior vena cava 28 into the right atrium 30 of the heart 33. FIG. 1 also shows the inferior vena cava 35, the left atrium 36, the right ventricle 37, the left ventricle 40, the atrial septum 41 that divides the two atria 30, 36, the ventricular vestibule VV, the right atrial appendage (RAA), and the tricuspid valve 42 between the right atrium 30 and right ventricle 37. The reader will appreciate that the view of FIG. 1 is simplified and somewhat schematic, but that nevertheless FIG. 1 and the other views included herein will suffice to illustrate adequately the placement and operation of embodiments of the present invention. The term "septum" shall be used throughout to generally refer to any portion of the heart separating two chambers (e.g. RA to LA, RV to LV). The leadless implantable medical device (LIMD) 300 is formed in accordance with an embodiment. The LIMD 300 may represent a pacemaker that functions in a DDD mode or a DDDR-mode, a cardiac resynchronization device, a cardioverter, a defibrillator and the like. When in DDD or DDDR-mode, the LIMD 300 may sense in two chambers, pace in two chambers and inhibit pacing in either chamber based on intrinsic events sensed in that chamber or in the other chamber. The LIMD 300 comprises a housing configured to be implanted entirely within a single local chamber of the heart. For example, the LIMD 300 may be implanted entirely and solely within the right atrium or entirely and solely within the right ventricle. Optionally, the LIMD 300 may be implanted entirely and solely within the left atrium or left ventricle through more invasive implant methods.

For convenience, hereafter the chamber in which the LIMD 300 is implanted shall be referred to as the "local" chamber. The local chamber includes a local chamber wall that is physiologically response to local activation events originating in the local chamber. The local chamber is at least partially surrounded by local wall tissue that forms or constitutes at least part of a conduction network for the associated chamber. For example, during normal operation, the wall tissue of the right atrium contracts in response to an intrinsic local activation event that originates at the sinoatrial (SA) node and in response to conduction that propagates along the atrial wall tissue. For example, tissue of the right atrium chamber wall in a healthy heart follows a conduction pattern, through depolarization, that originates at the SA node and moves downward about the right atrium until reaching the atria ventricular (AV) node. The conduction pattern moves along the chamber wall as the right atrium wall contracts.

The term "adjacent" chamber shall refer to any chamber separated from the local chamber by tissue (e.g., the RV, LV and LA are adjacent chambers to the RA; the RA and LV are adjacent chambers to the LA; the RA and RV are adjacent to one another; the RV and LV are adjacent to one another, and the LV and LA are adjacent to one another).

The local chamber (e.g., the right atrium) has various tissue of interest, such as a septum, that separate the local chamber from the adjacent chambers (e.g., right ventricle, left atrium, left ventricle). In certain portions or segments of the septum, segments of the septum, behave in physiologically different manners. For example, in certain segments of the septum for the right atrium, even during normal healthy operation, the septum wall tissue does not propagate the conduction in the same manner or pattern as in a majority of the wall tissue of the right atrium wall. For example, septum wall tissue in the right atrium, referred to as the ventricular vestibule tissue, does not behave physiologically in the same manner as the non-septum atrial wall tissue. Instead, the right ventricular vestibule tissue is physiologically coupled to the wall tissue in the right ventricle and in accordance therewith exhibits a conduction pattern that follows the conduction pattern of the right ventricular wall tissue. The right ventricular vestibule tissue is one example of a septum segment that partially separates a local chamber (e.g., the right atrium) from an adjacent chamber (e.g., right ventricle), yet is physiologically coupled to conduction in the adjacent chamber (e.g., right ventricle).

In the example of FIG. 1, the LIMD 300 is implanted in an area near different regions of tissue that follow the conductive pattern of different chambers of the heart. Optionally, the LIMD 300 may be implanted such that at least one electrode on the base of the LIMD 300 engages tissue that is part of the conductive network of the one chamber, while at least one other electrode projects from the base into tissue that is part of the conductive network of another chamber. For example, when the LIMD 300 may be implanted within or near the triangle of Koch in an area adjacent the ventricular vestibule. The conductive network of the tissue in the ventricular vestibule follows the conductive pattern of the right ventricle. Therefore, the LIMD 300 may be implanted near the edge of the triangle of Koch such that one or more proximal electrodes, extending from the LIMD 300, are electrically coupled to the conductive network of the right atrium, while one or more other distal electrodes, extend diagonally to become electrically coupled to the conductive network of the right ventricle (e.g., the ventricular vestibule). Optionally, the LIMD 300 may be positioned with the base located against the RA wall above the mitral valve, but with a distal electrode that projects into the septum to ventricular tissue of the right or left ventricle.

Figure 3A:
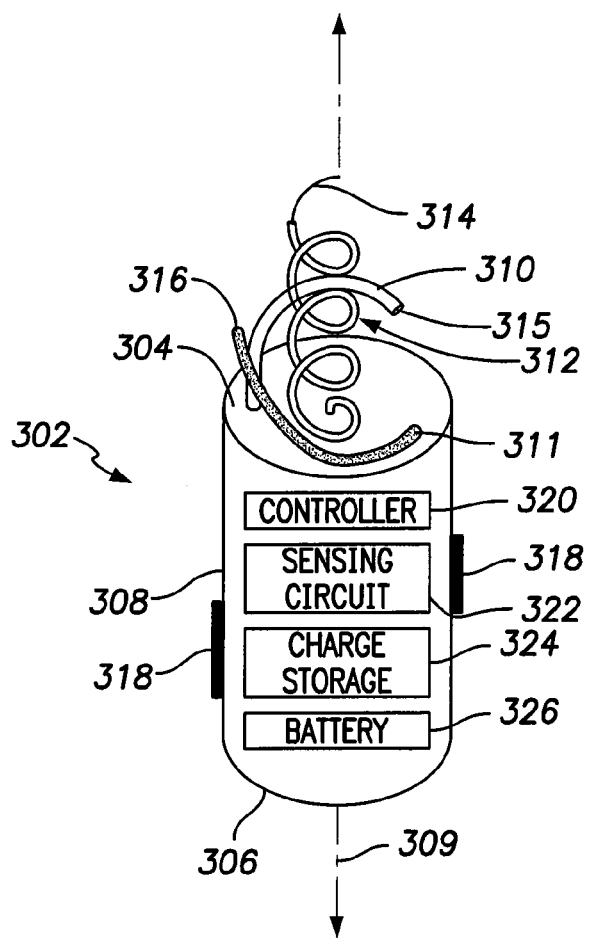
FIG. 3A illustrates a side perspective view of the LIMD of FIG. 1 oriented with the base facing upward to illustrate electrodes in more detail.
Figure 3B:
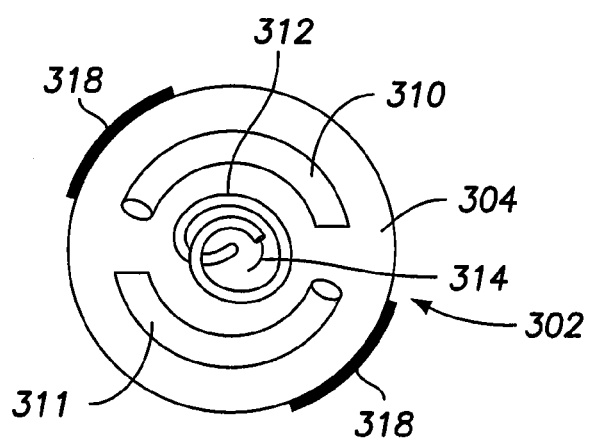
FIG. 3B illustrates a bottom plan view of the LIMD of FIG. 3A.

FIGS. 3A and 3B illustrate the LIMD 300 in more detail. FIG. 3A illustrates a side perspective view of the LIMD 300 of FIG. 1 oriented with the base 304 facing upward to illustrate electrodes 310-312 in more detail. FIG. 3B illustrates a bottom plan view of the LIMD 300. The LIMD 300 comprises a housing 302 having a proximal base 304, a distal top end 306, and an intermediate shell 308 extending between the proximal base 304 and the distal top end 306. The shell 308 is elongated and tubular in shape and extends along a longitudinal axis 309.

The base 304 includes one or more electrodes 310-312 securely affixed thereto and projected outward. For example, the outer electrodes 310, 311 may be formed as large semi-circular spikes or large gauge wires that wrap only partially about the inner electrode 312. The electrodes 310, 311 may be located on opposite sides of, and wound in a common direction with, the inner electrode 312. The first or outer electrodes 310, 311 are provided directly on the housing 302 of the LIMD 300 at a first position, namely at or proximate a periphery of the base 304 of the housing. The outer electrodes 310, 311 are positioned near the periphery of the base 304 such that, when the LIMD 300 is implanted in the local chamber (e.g., right atrium), the outer electrodes 310, 311 engage the local chamber wall tissue at tissue of interest for a local activation site that is near the surface of the wall tissue, and that is within the conduction network of the local chamber. The outer electrodes 310, 311 are physically separated or bifurcated from one another and have separate distal outer tips 315, 316. The outer electrodes 310, 311 are electrically joined to one another (i.e., common), but are electrically separated from the inner electrode 312.

The second or inner electrode 312 is also provided directly on the housing 302 of the LIMD 300 at a second position, namely at or proximate to a central portion of the base 304 of the housing. The inner electrode 312 is positioned near the center of the base 304 and is elongated such that, when the LIMD 300 is implanted in the local chamber, the inner electrode 312 extends a majority of the way through the wall tissue (e.g. septum) until reaching tissue of interest near the adjacent chamber wall. The inner electrode 312 is inserted to a depth such that a distal tip thereof is located at tissue of interest for an activation site that is physiologically coupled to wall tissue of the adjacent chamber (e.g. right ventricle). For example, the inner electrode 312 may extend until the distal tip extends at least partially through a septum to a position proximate to a distal wall tissue within the conduction network of the adjacent chamber. Optionally, the inner electrode 312 may be inserted at a desired angle until the distal end enters the ventricular vestibule. By located the distal tip of the inner electrode 312 at an adjacent chamber activation site, the inner electrode 312 initiates contraction at a distal activation site within the conduction network of the adjacent chamber without physically locating the LIMD 300 in the adjacent chamber. The inner and outer electrodes 310-312 may be formed as multiple cathode electrodes that are actively fixated to the myocardium. The outer cathode electrodes 310, 311 may be configured as screws with a large pitch (e.g. length between adjacent turns), large diameter and may have a length that is relatively short, while the inner electrode 312 is configured as a screw with a common or smaller pitch, small diameter and longer length. The screw shape of the outer electrodes 310, 311 is used to firmly adhere them to the cardiac tissue. The outer electrodes 310, 311 may have very little or no insulation material thereon to facilitate a good electrical connection to local wall tissue along the majority or the entire length of the outer electrodes 310, 311 for delivering stimulus pulses and sensing electrical activity in the local chamber where the LIMD 300 is located.

The inner electrode 312 is shaped in a helix or screw and is longer (e.g., extends a greater distance from the base) than the outer electrodes 310, 311. The inner electrode 312 is fashioned to an appropriate length that permits it to drill a predetermined distance into, or entirely through, the septum at the desired location. For example, the inner electrode 312 may be provided with a desired length sufficient to extend through, or to a desired distance into, a septum region separating two chambers of the heart. For example, the outer electrodes 310, 311 may contact atrial wall tissue within the triangle of Koch, while the inner electrode 312 extends diagonally along the septum into the ventricular vestibule.

The inner electrode 312 may be formed as a single conductive wire or a bundle of conductive wires, where a proximal portion of the wire is covered with insulation, while the distal tip 314 is covered with insulation and is exposed. By covering the proximal portion of the electrode 312 with insulation, this limits electrical conduction of the conductive wire to tissue surrounding the distal tip 314. When implanted, the distal tip 314 of the electrode is located far below the surface tissue of the chamber wall in which the LIMD 300 is located. As a consequence, the distal tip 314 of the inner electrode 312 directly engages or is located proximate to the surface tissue of an adjacent chamber wall. Hence, the distal tip will 314 senses electrical activity from the conductive network of the adjacent chamber that is representative of physiologic behavior (e.g., conduction pattern) of the adjacent chamber. Also, when delivering stimulus pulses, the distal tip 314 will deliver the pulses into the conductive network of the adjacent chamber wall.

The combination of the inner and outer screw type electrodes 310-312 also imparts extra mechanical stability to the LIMD 300, preventing unwanted torque and shear effects as the heart wall moves during contraction. Otherwise, such effects would otherwise predispose the LIMD 300 to dislodgement. Extraction could simply entail a combination of unscrewing of the two cathodes in conjunction with a slight tugging force directed away from the myocardial wall.

Optionally, a single anode electrode or multiple anode electrodes 318 may be provided. The anode electrode(s) 318 may be located along one or more sides of the shell 308, and/or on the top end 306 of the LIMD 300.

The LIMD 300 includes a charge storage unit 324 and sensing circuit 322 within the housing 302. The sensing circuit 322 senses intrinsic activity, while the change storage unit 324 stores high or low energy amounts to be delivered in one or more stimulus pulses. The electrodes 310-312 may be used to deliver lower energy or high energy stimulus, such as pacing pulses, cardioverter pulse trains, defibrillation shocks and the like. The electrodes 310-312 may also be used to sense electrical activity, such as physiologic and pathologic behavior and events and provide sensed signals to the sensing circuit 322. The electrodes 310-312 are configured to be joined to an energy source, such as a charge storage unit 324. The electrodes 310-312 receives stimulus pulse(s) from the charge storage unit 324. The electrodes 310-312 may be the same or different size. The electrodes 310-312 are configured to deliver high or low energy stimulus pulses to the myocardium.

The LIMD 300 includes a controller 320, within the housing 302, to cause the charge storage unit 324 to deliver activation pulses through each of the electrodes 310-312 in a synchronous manner, based on information from the sensing circuit 322, such that activation pulses delivered from the inner electrode 312 are timed to initiate activation in the adjacent chamber. The stimulus pulses are delivered synchronously to local and distal activation sites in the local and distal conduction networks such that stimulus pulses delivered at the distal activation site are timed to cause contraction of the adjacent chamber in a predetermined relation to contraction of the local chamber. The inner and outer electrodes 310-312 are spaced radially and longitudinally apart from one another such that the local activation site (e.g., right atrium) and the distal activation side in the adjacent chamber (e.g., right ventricle) are sufficiently remote from one another within the heart's conductive network to initiate activation in different branches of the hearts conductive network in a time relation that corresponds to the normal hemodynamic timers (e.g. AV delay).

Figure 2:
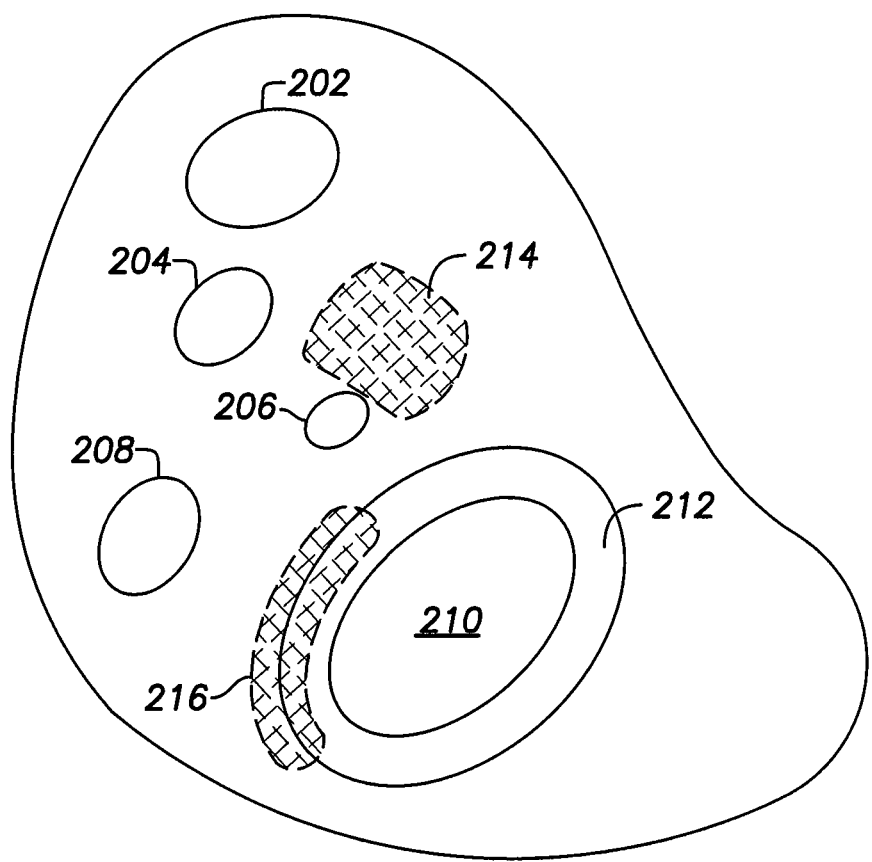
FIG. 2 illustrates a right anterior oblique view representing the interior surface of the right atrium wall.

FIG. 2 illustrates a right anterior oblique view representing the interior surface of the right atrium wall. As shown in FIG. 2, the right atrium wall includes the superior vena cava (SVC) inlet 202, the fosa ovalis 204, coronary sinus 206, IVC 208, tricuspid valve 210 and tricuspid annulus 212 that surrounds the tricuspid valve 210. The LIMD 300 may be implanted in various locations within the RA. For example, the LIMD 300 may be implanted in region 214 which is located immediately adjacent the coronary sinus 206. Region 214 may be contained within the Triangle of Koch. For example, the LIMD 300 may be implanted in region 216 which may represent the ventricular vestibule in an area located adjacent the tricuspid valve 210 along a segment of the tricuspid annulus 212. Region 214 represents a local activation site in the local chamber wall at which contractions may be initiated when stimulus pulses are delivered to the surface tissue in the region 214. Region 216, constitutes a distal activation site at which contractions may be initiated in the right ventricle when stimulus pulses are delivered in the region 216.

The controller 320 may operate the LIMD 300 in various modes, such as in select pacemaker modes, select cardiac resynchronization therapy modes, a cardioversion mode, a defibrillation mode and the like. For example, a typical pacing mode may include DDIR, R, DDOR and the like, where the first letter indicates the chamber(s) paced (e.g., A: Atrial pacing; V: Ventricular pacing; and D: Dual-chamber (atrial and ventricular) pacing). The second letter indicates the chamber in which electrical activity is sensed (e.g., A, V, or D). The code O is used when pacemaker discharge is not dependent on sensing electrical activity. The third letter refers to the response to a sensed electric signal (e.g., T: Triggering of pacing function; I: Inhibition of pacing function; D: Dual response (i.e., any spontaneous atrial and ventricular activity will inhibit atrial and ventricular pacing and lone atrial activity will trigger a paced ventricular response) and O: No response to an underlying electric signal (usually related to the absence of associated sensing function)). The fourth letter indicates rate responsive if R is present.

As one example, the controller 320 may be configured with DDI, DDO, DDD or DDDR mode-capable and the LIMD 300 would be placed in the RA. The screw type electrodes 310, 311 are used to secure it in conductive branch region 214 (FIG. 2). Conductive branch region 214 is contained within the Triangle of Koch and is characterized by more ready activation of RA tissue compared to conductive branch region 216. When the LIMD 300 is secured in conductive branch region 216, it is possible to achieve Hisian/para-Hisian pacing from the RA and perform biventricular stimulation that is more consistent with normal physiology. It may be possible to also perform AV pacing from conductive branch region 216.

As one example, the conductive branch region 216 represents the adjacent chamber activation site within the ventricular vestibule. The inner electrode 312 delivers stimulus pulses to the ventricular vestibule to initiate activation in the right ventricle 37 of the heart. When the LIMD 300 is secured in the conductive branch region septum 216, the inner electrode 312 is located in a minor tissue portion that is non-responsive to the local events and local conduction occurring in the right atrium. The distal end 314 of the inner electrode 312 electrically engages the minor tissue portion that is responsive to non-local events and non-local conduction originating in another chamber.

The sensing circuit 322 receives sensed signals from one or more of the electrodes 310-312. The sensing circuit 322 discriminates between sensed signals that originate in the near field and in the far field. For example, the electrodes 310-311 sense electrical potential across small areas and thereby allow the sensing circuit 322 to discriminate between different sources of electrical signals. In one embodiment, the electrode spacing between electrodes 310, 311 is limited or minimized in order to achieve a select type of sensing such as bipolar sensing which limits or minimizes sensing of far field signals. For example, the electrode 310 may operate as an anode electrode and the electrode 311 may operate as a cathode electrode with a small separation there between such that when far field signals (e.g., signals from the right ventricle) reach the first and second electrodes these far field signals are sensed as a common mode signal with no or a very small potential difference between the electrodes.

In another example, an electrode 312 may be provided with a pair of electrically separate sensing regions thereon. The sensing regions may operate as an anode and as a cathode electrode with a small separation there between such that when far field signals (e.g., signals from the right atrium) reach the first and second sensing regions these far field signals are sensed as a common mode signal with no or a very small potential difference between the sensing regions.

The housing 302 also include a battery 326 that supplies power to the electronics and energy to the change storage unit 324.

Figure 3C:
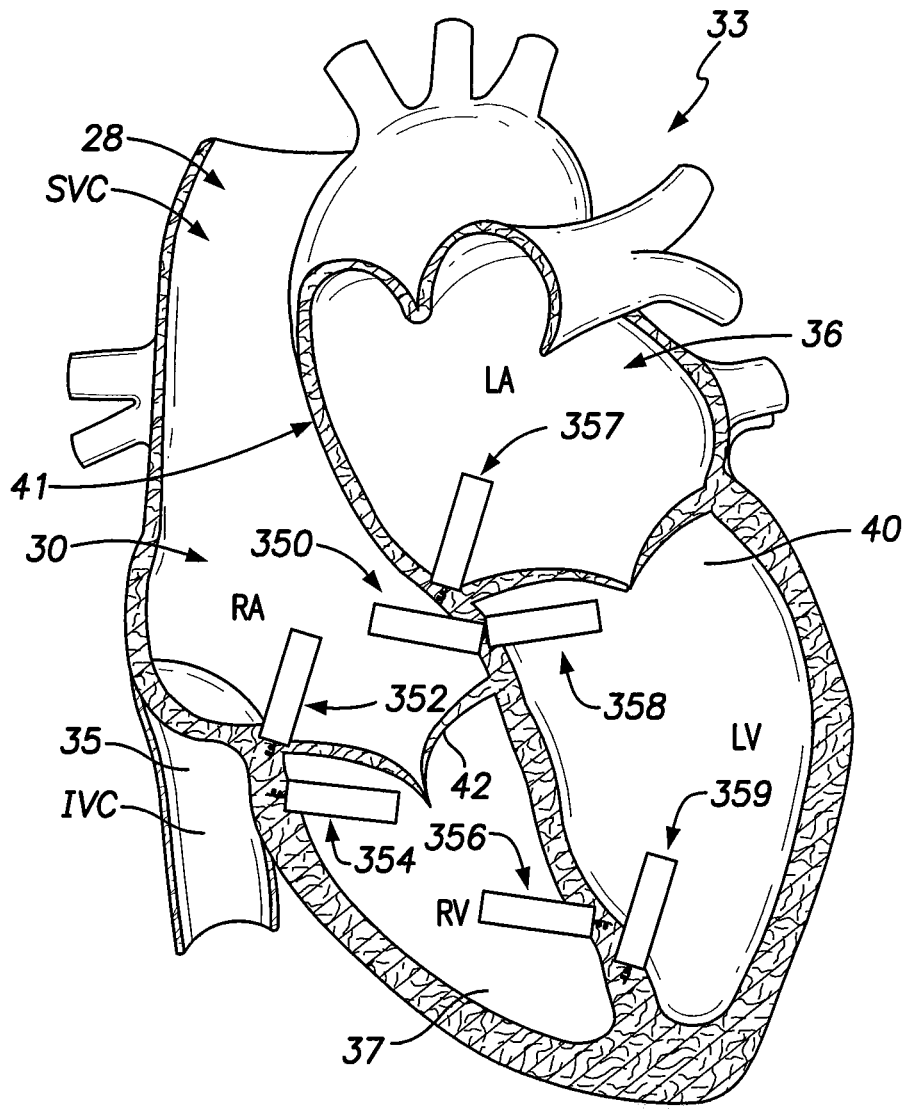
FIG. 3C illustrates examples of locations where an LIMD may be implanted.

FIG. 3C illustrates some of these possible configurations, namely at 350-356. The previous examples involve an LIMD implanted in the RA and capable of pacing the RV. Optionally, the LIMD may also be located in other locations. At 350, the LIMD is capable of HISian or para-HISian pacing to produce excitation of the RV and LV. When the LIMD is implanted at 352, the LIMD is able to provide RA/RV sensing and pacing from the RA. When the LIMD is implanted at 354, the LIMD is able to provide RA/RV sensing and pacing from the RV. When the LIMD is implanted at 356, the LIMD is able to provide RV/LV sensing and pacing from the RV. The LIMDs 357, 358, 359 afford LA/RA pacing and sensing, LV/RA pacing and sensing, and LV/RV pacing and sensing, respectively. These implementations produce excitation of the RV and LV in a manner more consistent with normal physiological function.

Figure 4A:
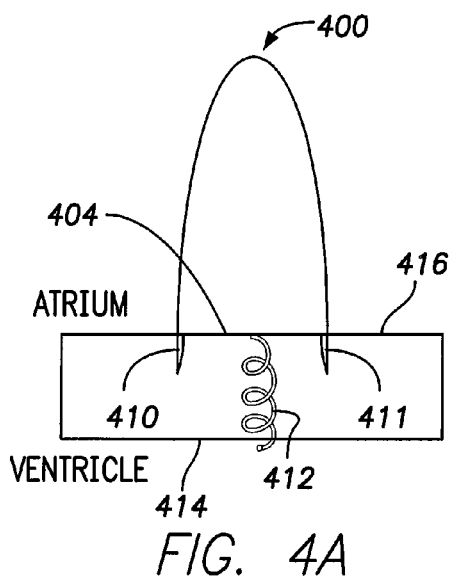

FIGS. 4A-4G illustrate various embodiments of fixation mechanisms that may be used with an LIMD 400. FIG. 4A illustrates a LIMD 400 that has a base 404 with spikes 410, 411 as cathode electrodes extending there from. The spikes 410, 411 are used to fixate the LIMD 400, as well as to deliver stimulus pulses and sense in the local chamber 416 (e.g. atrium). The LIMD 400 also includes an elongated cathode electrode 412 that is used for delivering stimulus pulses and for sensing electrical activity in the conduction network of the adjacent chamber 414 (e.g., the ventricle). The electrode 412 extends entirely through the chamber wall into the adjacent chamber 414. Optionally, the electrode 412 may extend near or up to, but not penetrate the wall tissue into the adjacent chamber 414.

Figure 4B:
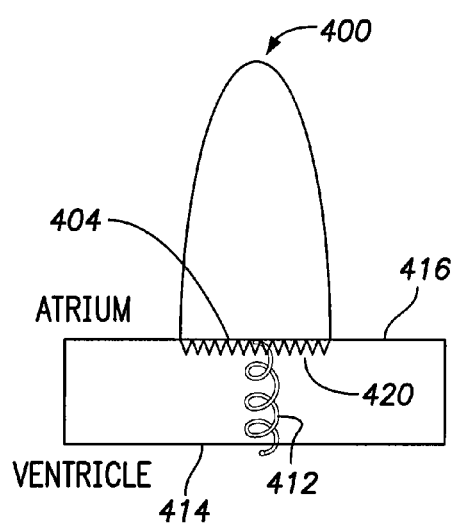
FIG. 4B illustrates a LIMD that has a base with serrated edges that project outward from the base.

FIG. 4B illustrates an LIMD 400 that has a base 404 with an electrode formed as serrated edges 420 that project outward from the base 404. The serrated edges 420 form a skirt encircling the base 404. The serrated edges 420 are electrically active and can be used for delivering stimulus pulses and for sensing conductive activity in the local chamber 416 as well as fixation. The LIMD 400 also includes an elongated cathode electrode 412 that is used for delivering stimulus pulses and for sensing conductive activity in the adjacent chamber 414 (e.g., the ventricle).

Figure 4C:
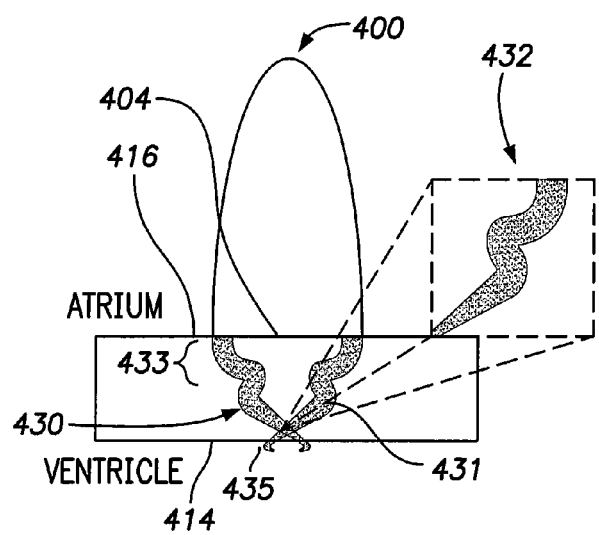
FIG. 4C illustrates a LIMD that has a base with a fixation mechanism similar to a pair of large diameter double-helix, but with a positive deflection near the base.

FIG. 4C illustrates an LIMD 400 that has a base 404 with electrodes formed as a fixation mechanisms 430, 431 similar to a pair of large diameter double-helix, but with a positive deflection 432 near the base 404. The purpose of this shape is to ease in the LIMD 400 during implant, but rendering unscrewing of the LIMD 400 very difficult due to its firm adhering to the wall. There may also be a single helix that varies in diameter or pitch from the proximal end to the distal end, which ensures ease of insertion at implant but causes detachment to be more difficult as tissue conforms to the helix's shape. The fixation mechanism 430 enclosed in insulation except for a proximal region 433 that is exposed and is electrically active in a proximal region near the base 404 in order to deliver stimulus pulses and to sense conductive activity in the local chamber 416. The fixation mechanism 431 is covered in insulation except for a distal region 435 that is exposed and is electrically active near the distal end remote from the base 404 in order to deliver stimulus pulses and to sense conductive activity in the adjacent chamber 414 (e.g., the ventricle).

Figure 4D:
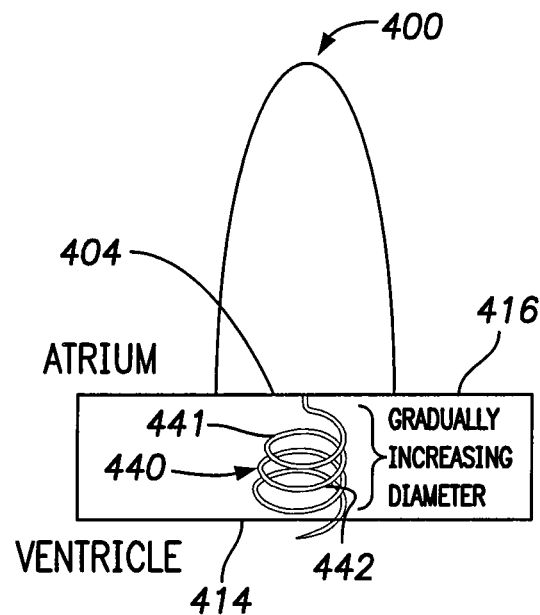
FIG. 4D illustrates a LIMD that has a base with a fixation mechanism that has a screw wire with different thickness at the proximal and distal ends.

FIG. 4D illustrates an LIMD 400 that has a base 404 with a fixation mechanism 440 that has a screw non-circular shape with different cross-sectional thicknesses at the proximal and distal ends 441, 442. By varying the cross sectional thickness at different locations along the fixation mechanism 440, this will afford better fixation of the LIMD 400. The cross-section may gradually increase or step-wise increase along the length of the mechanism 440 with greater distance from the base 404. For example, the fixation mechanism 440 may exhibit progressively widening cross-section toward the distal end 442 to afford better fixation.

Figure 4E:
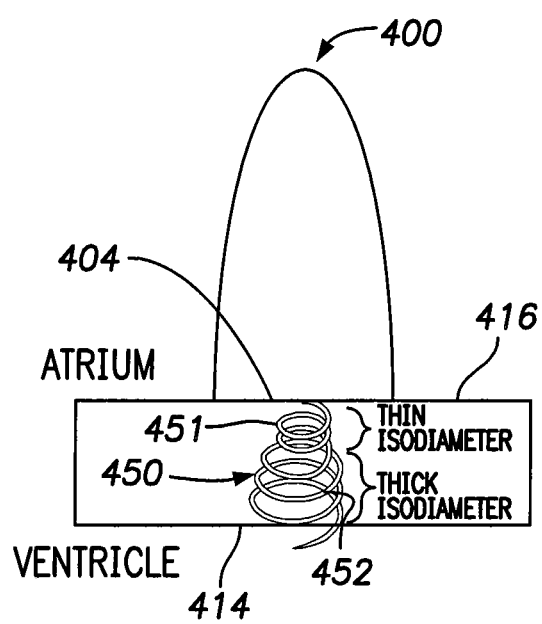
FIG. 4E illustrates a LIMD that has a base with a fixation mechanism that has a screw wire with different diameter at the proximal and distal ends.

FIG. 4E illustrates an LIMD 400 that has a base 404 with a fixation mechanism 450 that has a screw wire shape with different circular diameter at the proximal and distal ends 451, 452. By varying the wire diameter at different locations along the fixation mechanism 450, this will afford better fixation of the LIMD 400. The diameter of the wire may gradually increase or step-wise increase along the length of the mechanism 450 with greater distance from the base 404. The fixation mechanism 450 is formed with two isodiametric sections at the proximal and distal ends 451, 452 which are used to secure the LIMD 400. For example, the proximal end 451 may be thinner in diameter, while the distal end 452 is thicker in diameter.

Figure 4F:
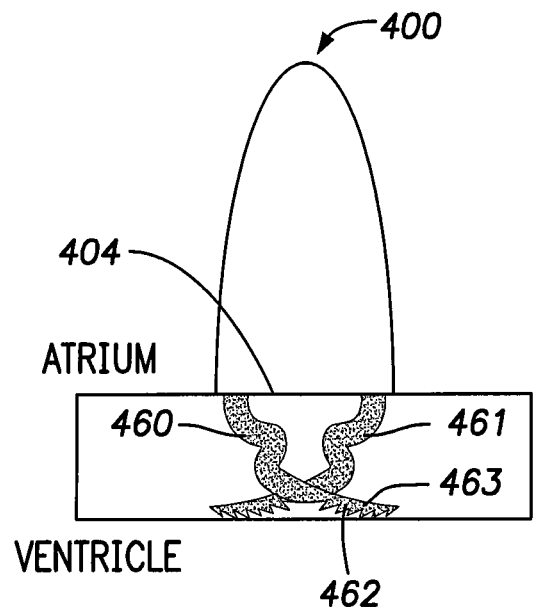
FIG. 4F illustrates a LIMD with a variation in the fixation mechanism shown in FIG. 4C.

FIG. 4F illustrates an LIMD 400 with a variation in the fixation mechanism 430, 431 shown in FIG. 4C. In FIG. 4F, the LIMD 400 includes fixation mechanisms 460, 461 with the distal ends 463 of the large double-helices having serrated edges 462 that prevent the LIMD 400 from unscrewing out of the heart chamber wall.

Figure 4G:
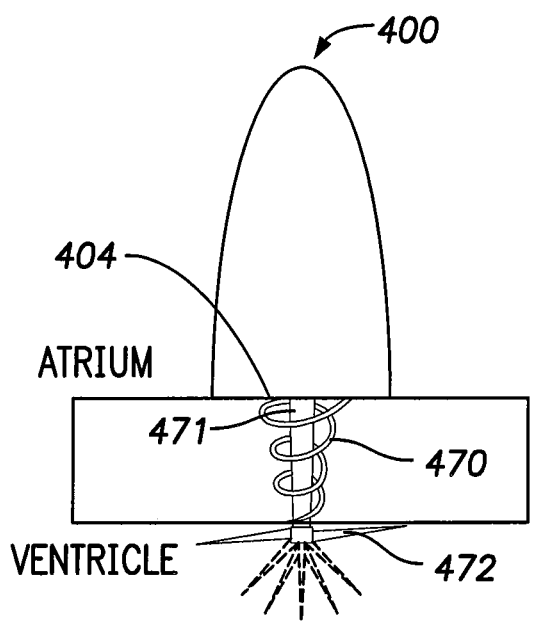
FIG. 4G illustrates a LIMD with a helical cathode electrode that surrounds a long spike electrode.

FIG. 4G illustrates an LIMD 400 with a helical cathode electrode 470 that surrounds a long spike electrode 471. Once implanted, the spike electrode 471 deploys a small mesh 472 similar in shape to an umbrella. The mesh 472 helps secure the LIMD 400 on both ends of the chamber wall.

Optionally, the LIMD 400 may have a single helical active-fixation mechanism that contains one or more passive electrodes on the LIMD 400 body that remain in the heart chamber where the LIMD 400 is implanted. The electrode could be brought into contact with the myocardium when the fixation is engaged. The electrodes shown in FIGS. 4A-4G may be cathodes, anodes or one of each. Optionally, an anode or cathode may be provided on the housing of the LIMD 400.

Figure 5A:
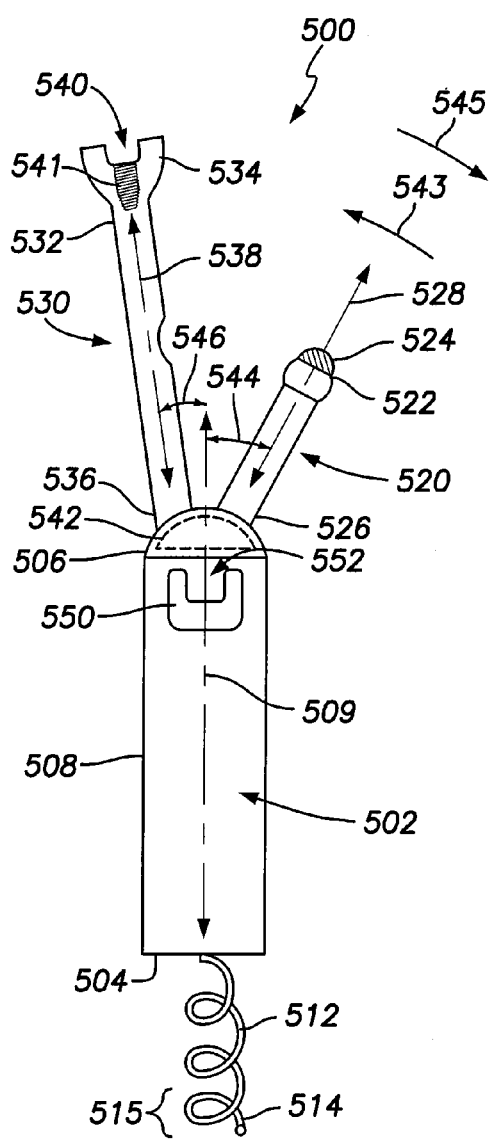
FIG. 5A illustrates a LIMD formed in accordance with an alternative embodiment, including an appendage arm and a stabilizer arm.

FIG. 5A illustrates an LIMD 500 formed in accordance with an alternative embodiment. The LIMD 500 includes a body or housing 502 having a shell 508 that hermetically encloses the electronics, controller, battery, charge storage unit, and all other electrical components of the LIMD 500. The housing 502 has a proximal base 504 and a distal top end 506, with the intermediate shell 508 extending there between. The shell 508 is elongated and may be tubular in shape to extend along a longitudinal axis 509. The base 504 includes at least one electrode 512. The electrode 512 may be a helical shaped screw to actively secure the base 504 at a desired site within a selected local chamber of the heart. The electrode 512 includes a conductor that is surrounded by insulation along the majority of the length thereof, but exposes the distal tip 514 of the conductor, such that the electrode 512 only delivers stimulus pulses and senses electrical activity in the region denoted at 515 which corresponds to an distal activation site proximate an adjacent chamber wall (and distal from the local chamber in which the LIMD 500 is implanted).

The LIMD 500 further includes an appendage arm 520 pivotally connected to and extending outward from the top end 506. The appendage arm 520 includes a distal end 522 upon which an electrode 524 is located. The electrode 524 may be a passive electrode that is configured to simply rest against a select activation site. Alternatively, the electrode 524 may be an active fixation electrode that is configured to be secured to the tissue at the activation site (e.g. through a helix, spike, serrated edge, barb, and the like).

The appendage arm 520 includes a proximal end 526 that is rotatably coupled through a hinge assembly 542 to the top end 506 of the housing 502. The appendage arm 520 extends along an appendage axis 528 and rotates along the appendage rotation arc 544 between limits. The hinge assembly 542 is configured to permit the appendage arm 520 to rotate from a collapsed installation position to a deployed implanted position. When in the collapsed position, the appendage arm 520 is rotated in the direction of arrow 543 until the appendage axis 528 forms a very small acute angle, or is oriented substantially parallel to, a longitudinal axis 509 of the shell 508 of the LIMD 500. When in the deployed position, the appendage arm 520 rotates in the direction of arrow 545 until reaching a fully deployed outer limit of the arc of rotation as defined by the hinge assembly 542. When fully deployed, the appendage axis 528 projects outward at a larger acute angle (e.g. 10-150°) from the longitudinal axis 509 of the shell 508. The outer limit of the deployed position for the appendage arm 520 is controlled by the rotation range permitted at the hinge assembly 542 and may have spring tension tensioning it with respect to the stabilizer arm or the housing 502.

The LIMD 500 also includes a stabilizer arm 530 having a distal end 532 and a proximal end 536. The distal end 532 is formed integral with a pusher cup 534 that includes some type of pusher reception feature, such as a pusher receptacle 540. The pusher cup 534 and receptacle 540 are configured to receive an external pusher tool that is used by the physician when implanting the LIMD 500 (as explained below in more detail). As one example, the pusher receptacle 540 may include a threaded recess 541 that is configured to threadably and securely receive a tip of the pusher tool to ensure a secure attachment to the pusher tool during installation. Once the LIMD 500 is fully implanted, the tip of the pusher tool is unscrewed from the threaded receptacle 541. An expandable collet may be used, instead of a screw to attach the pusher tool to the stabilizer arm 530.

The stabilizer arm 530 is rotatably secured, at its proximal end 536, to the hinge assembly 542 to permit the stabilizer arm 530 to rotate along arc 546. The stabilizer arm 530 may be rotated between a collapsed installation position at which the stabilizer axis 538 is arranged at a very small acute angle or substantially parallel to the longitudinal axis 509. Once implanted, the stabilizer arm 530 is then permitted to rotate outward along arc 546 to a deployed position such that the stabilizer axis 538 forms a larger acute angle (e.g. 10-150°) with respect to the longitudinal axis 509. The hinge assembly 542 controls the range of rotation afforded to the stabilizer arm 530 and may have spring tension tensioning it with respect to the appendage arm 520 or the housing 502.

At least one of the stabilizer arm 530 and appendage arm 520 may be constructed to have a core structure that is torque and compression resistant such that when the pusher tool is rotated or moved longitudinally, the stabilizer arm 530 and/or appendage arm 520 conveys rotational and longitudinal force from the pusher tool to the housing of the LIMD 500. For example, the core structure may include a metal (e.g. stainless steel) braid encased in a biocompatible material, such as PTFE, ETFE or silicon rubber. The braid may have a hollow core in which insulated conductors run between electrodes and the LIMD 500. In one arrangement the conductors may be wound about one another in a helical manner. The conductors extend along a core and the conductors are radially surrounded by an elongated braid. The braid may be made of steel or wire mesh, or have a honeycomb pattern that resists compression or IC device extension along the length of the IC device extension body. The braid is flexible in a lateral direction in order to be bent side to side during implant and following implant. The mesh or honeycomb configuration of the braid affords strong resistance to torque about the length of the IC device extension body when turned in the rotational direction about the longitudinal direction. It is desirable to be resistant to torque in order that, during implant, when a rotational force is applied to one end of the IC device extension body, substantially all of such rotational force is conveyed along the length of the IC device extension body to the opposite end. As explained hereafter, the braid facilitates delivery of rotational forces and longitudinal pressure to the LIMD.

Optionally, the stabilizer arm 530 may be fixedly secured to the distal end 506 of the LIMD 500, such that the stabilizer arm 530 does not rotate relative to the longitudinal axis 509. Instead, in this alternative embodiment, the stabilizer arm 530 is rigidly secured to the distal end 506 and may be oriented such that the stabilizer axis 530 extends directly parallel or at an angle to the longitudinal axis 509 at all times, during installation and after deployment.

As a further option, a pusher cup or multiple pusher cups 550 may be provided about the exterior surface of the shell 508 or on the distal top end 506. The pusher cup 550 includes a pusher receptacle 552 configured to receive the tip of a pusher tool that is used during implantation. The pusher cup 550 may be provided in place of, or in addition to, the pusher cup 534. For example, the stabilizer arm 530 may be entirely removed, in which case the pusher cup 550 may be provided on the side or top end 506 of the housing 502. Alternatively, when the stabilizer arm 530 is included, but is too flexible to convey rotational and/or longitudinal force onto the housing 502, then the pusher cup 550 may be included. As a further option, pusher cups 534, 550 may both be included such as when it is desirable to maintain secure connections to the housing 502 and the appendage arm 520 and stabilizer arm 530 while manipulated and navigated to respective implanted positions. For example, once the LIMD 500 is secured to the chamber wall, the introducer may be partially removed, yet one pusher tool or stylet may remain secured to the pusher cup 550 to maintain the LIMD 500 in a desired position and orientation while a second tool manipulates the appendage arm 520 and stabilizer arm 530 to implant positions. In this manner, the tool or stylet in pusher cup 550 prevents excess forces from being applied to the electrode 512 while the arms 520, 530 are navigated to installed positions. Further, the tool or stylet may remain in pusher cup 550 until a separate tool is disconnected from pusher cup 534.

Optionally, a third pusher cup could be located on the distal end of the appendage arm 520 to afford direct control over positioning of the electrode 524.

Figure 5B:
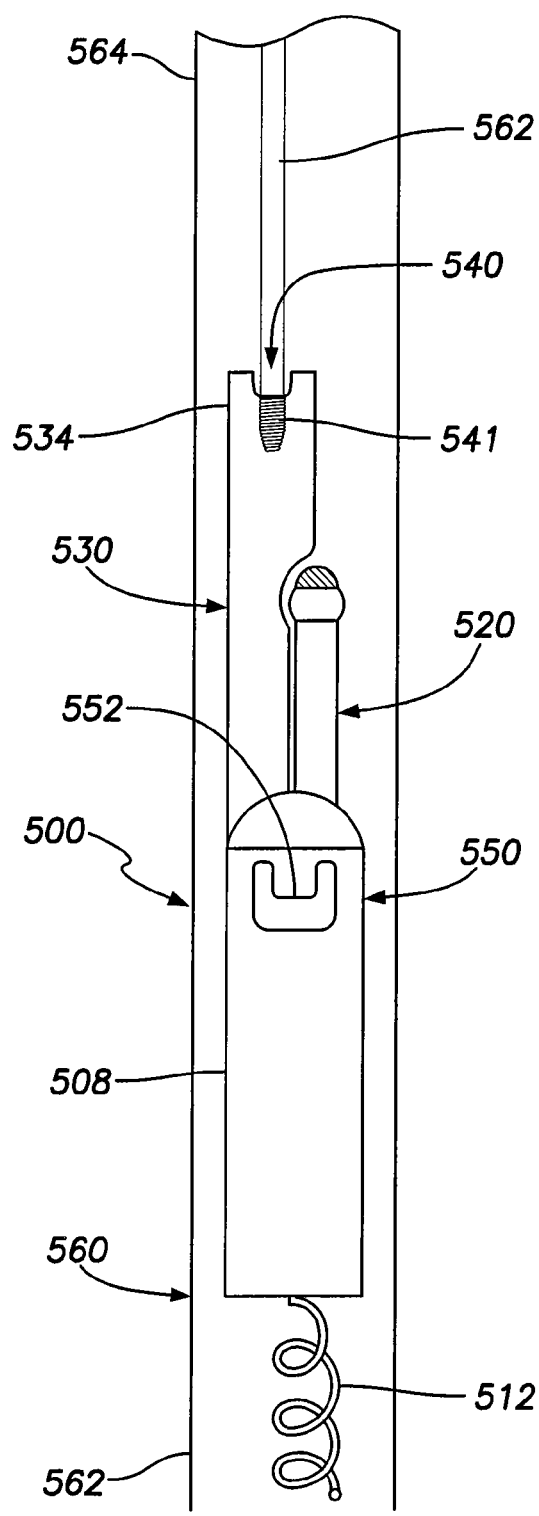
FIG. 5B illustrates the LIMD of FIG. 5A during installation, while rotated within an introducer.

FIG. 5B illustrates the LIMD 500 of FIG. 5A during installation, while located within an introducer 560. The introducer has a distal end 562 that is open to permit the LIMD 500 to be implanted and deployed there through. The introducer 560 includes a proximal end 564 along which a pusher or other form of tool (e.g. a stylet) is used guide the LIMD 500 into position. As shown in FIG. 5B, the stabilizer arm 530 and appendage arm 520 are contracted in their collapsed position to define an outer envelope substantially no greater than the outer envelope of the body 508 of the LIMD 500. The pusher device 562 may engage one or both of the pusher receptacle 540 in the pusher cup 534 and/or the pusher receptacle 552 and the pusher cup 550. During implantation, the pusher or stylet 562 is securely attached at the cup 534 to guide the LIMD 500 to its activation site. Once the electrode 512 is located against the desired tissue at the activation site, the pusher or stylet 562 may then be rotated to similarly cause the LIMD 500 and electrode 512 to rotate until securely affixed within the select tissue. As one example, the 540 and/or 552 may have a noncircular cross section as viewed from the top down (e.g. a rectangular triangle, hexagon, or other polygon shape) such that when the pusher or stylet 562 is rotated, it remains securely fixed within the 540 to induce rotation at the electrode 512.

Figure 6A:
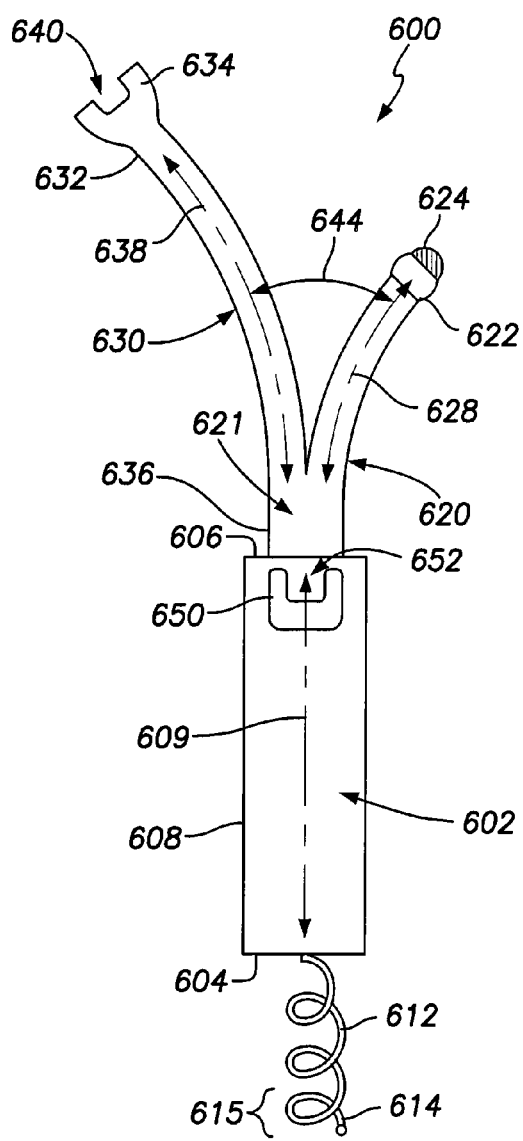
FIG. 6A illustrates a LIMD formed in accordance with an alternative embodiment, in which the appendage arm and stabilizer arm are configured in a manner different than those of FIG. 5A.

FIG. 6A illustrates an LIMD 600 that resembles the LIMD 500, except that the appendage arm 620 and stabilizer arm 630 are configured in a manner different than those of FIG. 5A. In the embodiment of FIG. 6A, the stabilizer arm 630 and appendage arm 620 are integrally joined with one another in a base area 621, but are formed of a flexible material that has a desired preformed resting shape, corresponding to the deployed configuration illustrated in FIG. 6A. When in the deployed position, the stabilizer arms 628, 630 are flared outward away from one another by an angle denoted at 644. The stabilizer arms 628, 630 may be formed with shape memory characteristics that allow the arms to transform between a collapsed state, in which the arms assumes a substantially linear shape, and an expanded state, in which the arm assumes a multiple curved shape.

The appendage arm 620 and stabilizer arm 630 have a common proximal end 636 that is secured to the top end 606 of the body 602. The appendage arm 620 has a distal end 622 with an electrode 624 thereon as configured to passively or actively engage tissue at a desired activation site. The stabilizer arm 630 has a distal end 632 at which a pusher cup 634 is formed integral therewith. The pusher cup 634 includes a pusher receptacle 640 that is configured to receive a pusher tool during installation. During installation, the appendage arm 620 and stabilizer arm 630 are flexed inward to collapse against one another such that the angle 644 is very small or approximately zero in order that the appendage axis 628 and stabilizer axis 638 extend substantially parallel to the longitudinal axis 609 of the LIMD 600. When the appendage and stabilizer arms 620, 630 are collapsed against one another, the outer envelope thereof is no greater than the outer envelope of the shell 608 to provide a form factor small enough to be received within an introducer for installation in a desired chamber of the heart.

The LIMD 600 includes a body or housing 602 having a shell 608 that hermetically encloses the electronics, controller, battery, charge storage unit, and all other electrical components of the LIMD 600. The housing 602 has a proximal base 604 and a distal top end 606, with the intermediate shell 608 extending there between. The shell 608 is elongated and may be tubular in shape to extend along a longitudinal axis 609. The base 604 includes at least one electrode 612. The electrode 612 may be a helical shaped screw to actively secure the base 604 at a desired site within a selected local chamber of the heart. The electrode 612 includes a conductor that is surrounded by insulation along the majority of the length thereof, but exposes the distal tip 614 of the conductor, such that the electrode 612 only delivers stimulus pulses and senses electrical activity in the region denoted at 615 which corresponds to an distal activation site proximate to an adjacent chamber wall (and distal from the local chamber in which the LIMD 600 is implanted).

The LIMD 600 further includes an appendage arm 620 pivotally connected to and extending outward from the top end 606. The appendage arm 620 includes a distal end 622 upon which an electrode 624 is located. The electrode 624 may be a passive electrode that is configured to simply rest against a select activation site. Alternatively, the electrode 624 may be an active fixation electrode that is configured to be secured to the tissue at the activation site (e.g. through a helix, spike, serrated edge, barb and the like).

The LIMD 600 also includes a stabilizer arm 630 having a distal end 632 and a proximal end 636. The distal end 632 is formed integral with a pusher cup 634 that includes some type of pusher reception feature, such as a pusher receptacle 640. The pusher cup 634 and receptacle 640 are configured to receive an external pusher tool that is used by the physician when implanting the LIMD 600 (as explained below in more detail). As one example, the pusher receptacle 640 may include a threaded recess 641 that is configured to threadably and securely receive a tip of the pusher tool to ensure a secure attachment to the pusher tool during installation. Once the LIMD 600 is fully implanted, the tip of the pusher tool is unscrewed from the threaded receptacle 641.

The stabilizer arm 630 may be flexed between a collapsed installation position at which the stabilizer axis 638 is arranged at a very small acute angle or substantially parallel to the longitudinal axis 609. Once implanted, the stabilizer arm 630 is then permitted to return to its flared state to a deployed position such that the stabilizer axis 638 forms a larger acute angle (e.g.)10-60° with respect to the longitudinal axis 609.

Optionally, the stabilizer arm 630 may be fixedly secured to the distal end 606 of the LIMD 600, such that the stabilizer arm 630 does not rotate relative to the longitudinal axis 609. Instead, in this alternative embodiment, the stabilizer arm 630 is rigidly secured to the distal end 606 and may be oriented such that the stabilizer axis 630 extends directly parallel to the longitudinal axis 609 at all times, during installation and after deployment.

As a further option, a pusher cup or multiple pusher cups 650 may be provided about the exterior surface of the shell 608. The pusher cup 650 includes a pusher receptacle 652 configured to receive the tip of a pusher tool that is used during implantation. As explained above in connection with FIG. 5A, one or more pusher cups may be provided in various locations.

Figure 6B:
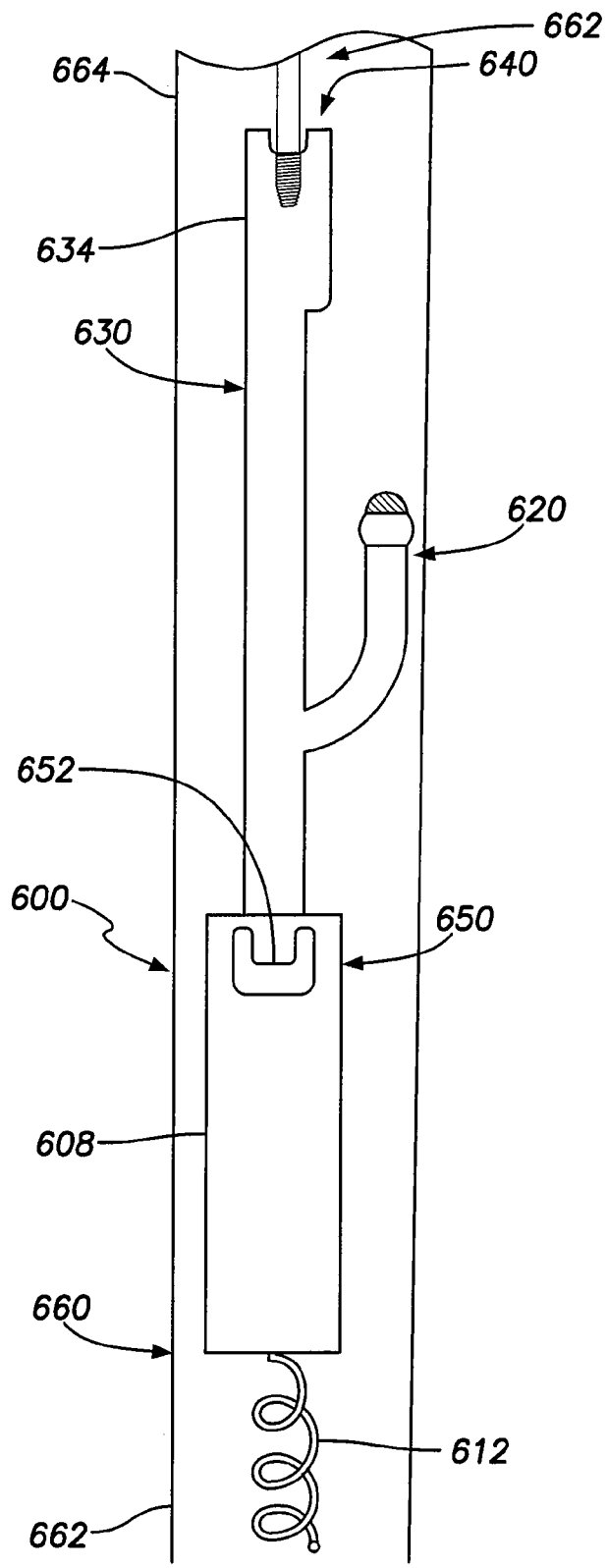
FIG. 6B illustrates the LIMD of FIG. 6A during installation, while located within an introducer.

FIG. 6B illustrates the LIMD 600 of FIG. 6A during installation, while located within an introducer 660. The introducer has a distal end 662 that is open to permit the LIMD 600 to be implanted and deployed there through. The introducer 660 includes a proximal end 664 along which a pusher or other form of tool (e.g. a stylet) is used guide the LIMD 600 into position. As shown in FIG. 6B, the stabilizer arm 630 and appendage arm 620 are contracted in their collapsed position to define an outer envelope substantially no greater than the outer envelope of the body 608 of the LIMD 600. The pusher device 662 may engage one or both of the pusher receptacle 640 in the pusher cup 634 and/or the pusher receptacle 652 and the pusher cup 650. During implantation, the pusher or stylet 662 is securely attached at the receptacle cup 634 to guide the LIMD 600 to its activation site. Once the electrode 612 is located against the desired tissue at the activation site, the pusher or stylet 662 may then be rotated to similarly cause the LIMD 600 and electrode 612 to rotate until securely affixed within the select tissue. As one example, the receptacle 640 and/or receptacle 652 may have a noncircular cross section as viewed from the top down (e.g. a rectangular triangle, hexagon, or other polygon shape) such that when the pusher or stylet 662 is rotated, it remains securely fixed within the receptacle 640 to induce rotation at the electrode 612.

Figure 7A:
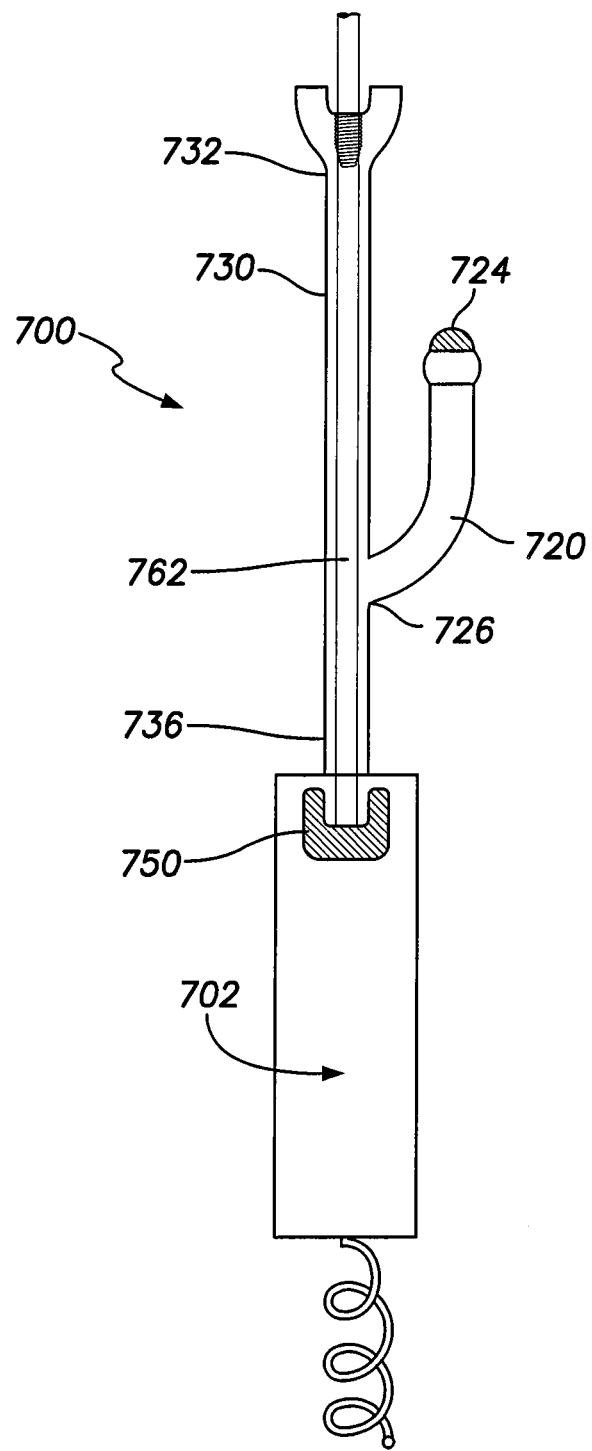
FIG. 7A illustrates an alternative embodiment for a LIMD in a collapsed installation configuration.
Figure 7B:
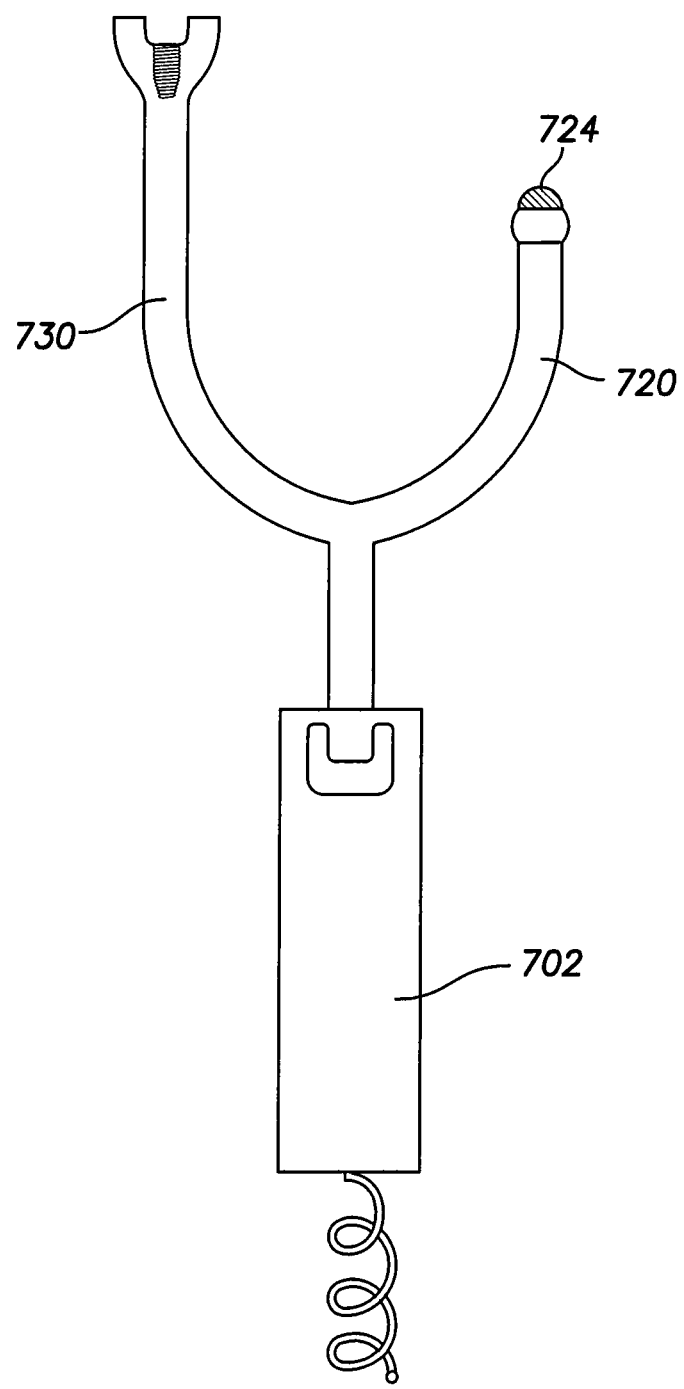
FIG. 7B illustrates the LIMD of FIG. 7A in a deployed flared position.

FIGS. 7A and 7B illustrate an alternative embodiment for an LIMD 700 when in the collapsed installation configuration (FIG. 7A) and in the deployed flared position (FIG. 7B). The LIMD 700 includes a stabilizer arm 730 having a distal and proximal end 732, 736. An appendage arm 720 is integrally formed with and extends outward at an intermediate position from, the stabilizer arm 730. The appendage arm 720 includes a proximal end 726 that is joined to the stabilizer arm 730 at an intermediate position away from the body 702 of the LIMD 700. The appendage arm 720 includes an electrode 724 on the distal end thereof. As shown in FIG. 7A, before deployment and while in the collapsed position, the appendage arm 720 does still slightly project outward beyond the outer envelope of the body 702, but the stabilizer arm 730 extends along the direction substantially parallel to the longitudinal axis of the body 702. In the example of FIG. 7A, the pusher cup 750 is located at the distal top end of the body 702. The stabilizer arm 730 has a hollow passage there through that receives a tool 762 that pushes the LIMD 700 to a desired deployed position. For example, the passage through the stabilizer arm 730 aligns with the pusher cup 750 in the distal top end such that the tool 762 is inserted into the passage until securely engaging the pusher cup 750. When in the passage, the tool 762 maintains the stabilizer arm 730 in a straight, elongated shape extending along the longitudinal axis of the tool 762.

Turning to FIG. 7B, once the LIMD 700 is implanted and the introducer and tool 762 removed, the stabilizer arm 730 and appendage arm 720 are permitted to flare outward to form a Y-shaped configuration. It should be recognized that the shape formed by the stabilizer arm 730 and appendage arm 720 after deployment may be modified and controlled during construction to achieve a desired final configuration when implanted. By removing the tool 762, the stabilizer arm 730 is permitted to return to its natural pre-formed shape.

Figure 5C:
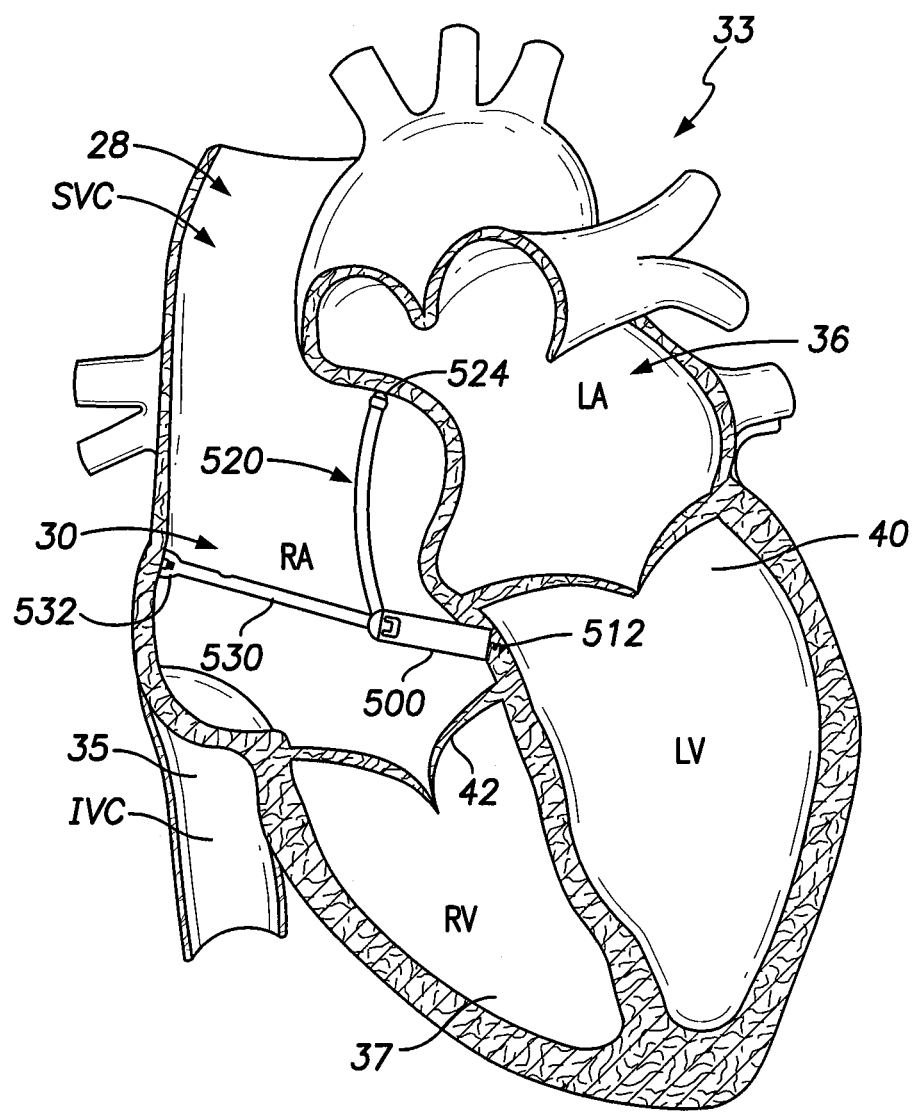
FIG. 5C illustrates the LIMD of FIG. 5A in an exemplary deployed position within a heart.

FIG. 5C illustrates the LIMD 500 in an exemplary deployed position. When deployed as illustrated in FIG. 5C, the LIMD 500 may be located directly against the ventricular vestibule. The electrode 512 is secured to the ventricular vestibule and/or extended to a point such that the distal end of the electrode 512 projects into or is located directly against the surface tissue of the right ventricle. The appendage arm 520 is flared to its deployed position to locate the electrode 524 against atrial tissue in the atrial appendage area. In the example of FIGS. 5A-5C, the electrode 524 is configured to simply be pressed against the tissue at the atrial appendage. Optionally, spikes or a serrated edge or other fixation means may be added to the electrode at 524 to further facilitate engagement to the tissue in the atrial appendage.

When deployed and in the flared position, the stabilizer arm 530 extends into the SVC and rests against the side of the SVC to provide stabilization for the overall positioning of the LIMD 500. It should be recognized, that throughout operation, as the right atrium moves during contraction, the stabilizer arm 530 and appendage arm 520 constantly pivot, rotate and/or flex to avoid interference with the normal mechanical movement of the right atrium.

Figure 6C:
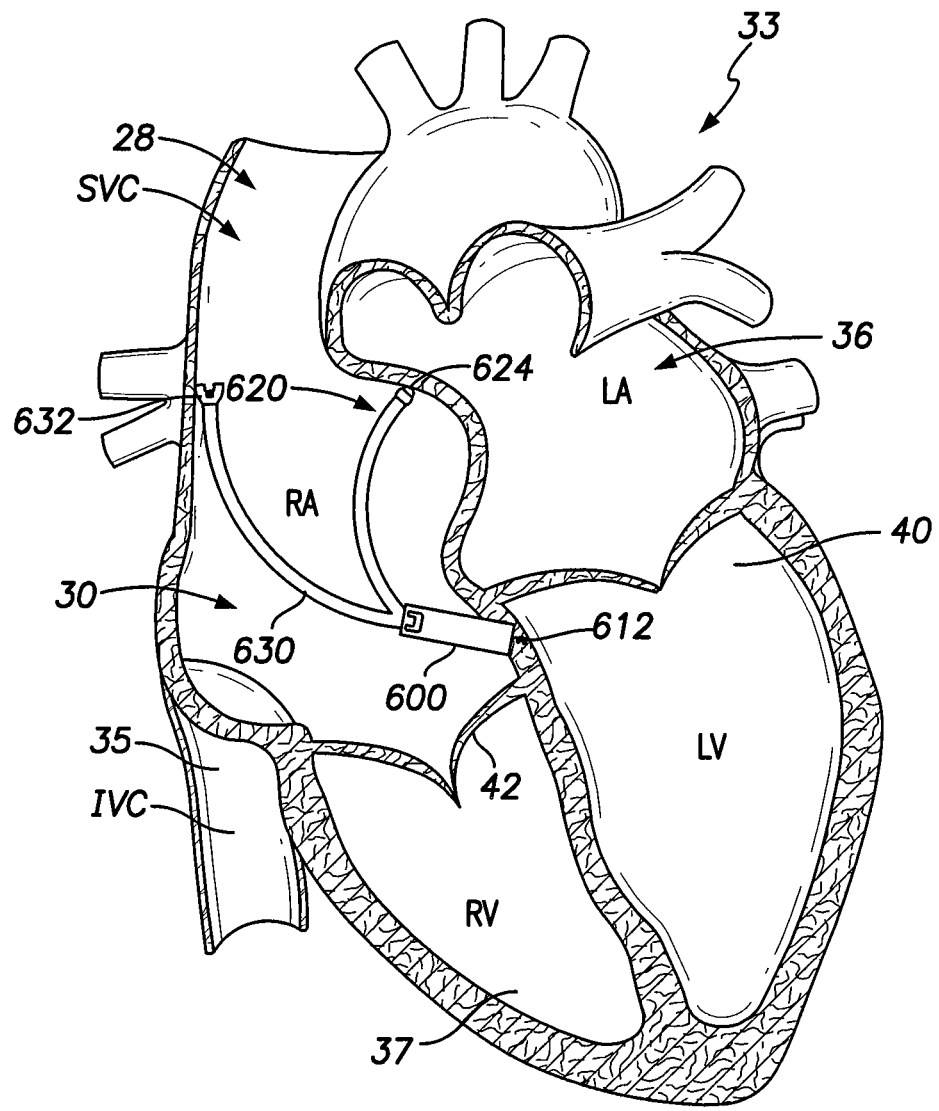
FIG. 6C illustrates the LIMD of FIG. 6A in an exemplary deployed position within a heart.

FIG. 6C illustrates an exemplary deployment of the LIMD 600 when located in the right atrium. The electrode 612 is securely affixed through the ventricular vestibule and/or locate the distal end thereof within or immediately adjacent the surface of the right ventricular wall. The appendage arm 620 is flared to a deployed position to locate the electrode 624 in the atrial appendage. The stabilizer arm 630 is also flared in the opposite direction to its deployed position such that the distal end 632 extends into and engages tissue within the SVC. As explained above, the appendage arm 620 and stabilizer arm 630 are flexible and will constantly move in connection with the mechanical contraction of the right atrium to avoid interference with the normal mechanical movement of the heart.

As shown in FIGS. 5A-5C, 6A-6C, and 7A-7B, the LIMD may be provided with two or more fixation mechanisms at the top end of the device body. One fixation mechanism, which is not electrically active, acts as to stabilize and passively-fixate the LIMD 300 in the superior vena cava (SVC). The other fixation mechanism is shorter but has an electrode at its tip and has the dual role of passive fixation to the RA appendage and pacing and sensing the RA. Additionally, the LIMD 300 has two or more possible configurations for attachment to the implant (and possibly explant) tool at either the end of the SVC stabilization fixation mechanism or at the side of the LIMD body. When the LIMD is affixed to the desired target site and the introducer (which protects blood vessels and myocardium from being damaged by the helical cathode) is removed, the passive fixation mechanisms swivel away from the longitudinal axis of the LIMD and contact their respective sites. The degree by which these fixation mechanisms swivel away from each other may be pre-determined or controlled by a ratcheting mechanism via the implant tool. Alternatively, the LIMD may use a stylet after affixation to the target site, which transmutes the morphology of the fixation mechanisms from a "J-shape" to a "U-shape," as shown in FIG. 7B.

In FIGS. 5C and 6C, the LLPM is affixed to the target site on the atrioventricular wall and is deployed in the RA. Here, it can be seen that there are three points of contact between the LIMD and myocardium, significantly reducing the possibility of dislodgement. In addition, dual chamber (e.g. DDD or DDDR mode) functionality is achieved via the RA appendage fixation mechanism (which paces and senses the RA) and the helical cathode electrode (which paces and senses the RV).

If dual-chamber pacing and sensing is achieved with a long helical fixation electrode covered proximally with insulation, it may be desirable to know when the helix has extended through the myocardium to the adjacent chamber. This may be determined using real-time impedance measurement between the helical tip electrode and another electrode. When the helical electrode is in pooled blood of any heart chamber, characteristic low impedance will be between it and any other electrode in the blood. As the helical electrode is screwed into the myocardium, impedance will rise. When the helix has been affixed sufficiently to break through the wall to the other chamber, impedance will drop. The changes in impedance may be used to know how far to screw in the helix, which portions of walls delineating heart chambers are an appropriate thickness for the helix, and whether any other spacer is needed to prevent the device from torqueing with the heart's mechanical motion.

Before disconnecting from the insertion tool, a pacing test provides an indication of the chamber paced and capture threshold. If the test shows that pacing is not occurring in the desired chamber or that thresholds are inappropriate, the tool may be used to remove the fixation and attempt to attach at another location.

For each attempt, the distance traversed by the lead's AV helix through the wall between the RA and RV between each turn of the screw may be closely controlled. Atrial and ventricular capture thresholds may be recorded with a pacing system analyzer (PSA) between each turn or at set degrees of rotation. The PSA may use the electrodes on the LIMD or may use electrodes on the exterior or outer end of the introducer to test for capture thresholds prior to affixing the LIMD in place. The distance between each turn may be generally between 0.5 to 2.0 mm. For example, all lead helical electrodes may be coated with an insulating material such as Parylene®-coated except for the most distal portion of the pitch of the screws (thus ensuring that only tissue near the tip is stimulated). For example, the helical electrode may be advanced in small increments, and after each increment, the PSA may then test for a capture. An interactive process may be repeated whereby the electrode is advanced and then the PSA determines if a capture threshold has been satisfied. This process is repeated until impulses from the distal electrode capture the ventricular tissue. Similarly, a capture test may be performed for the atrial electrode. The atrial electrode is adjusted until the PSA confirms atrial capture. In accordance with the foregoing, it is possible for an AV helical electrode on a lead to burrow from the RA and excite ventricular tissue. This allows a dual chamber mode-capable LIMD to have its main body located in the one chamber and pace and sense another chamber.

The term "distal" as used to describe wall tissue and activation sites, is used with respect to the local chamber.

Figure 8:
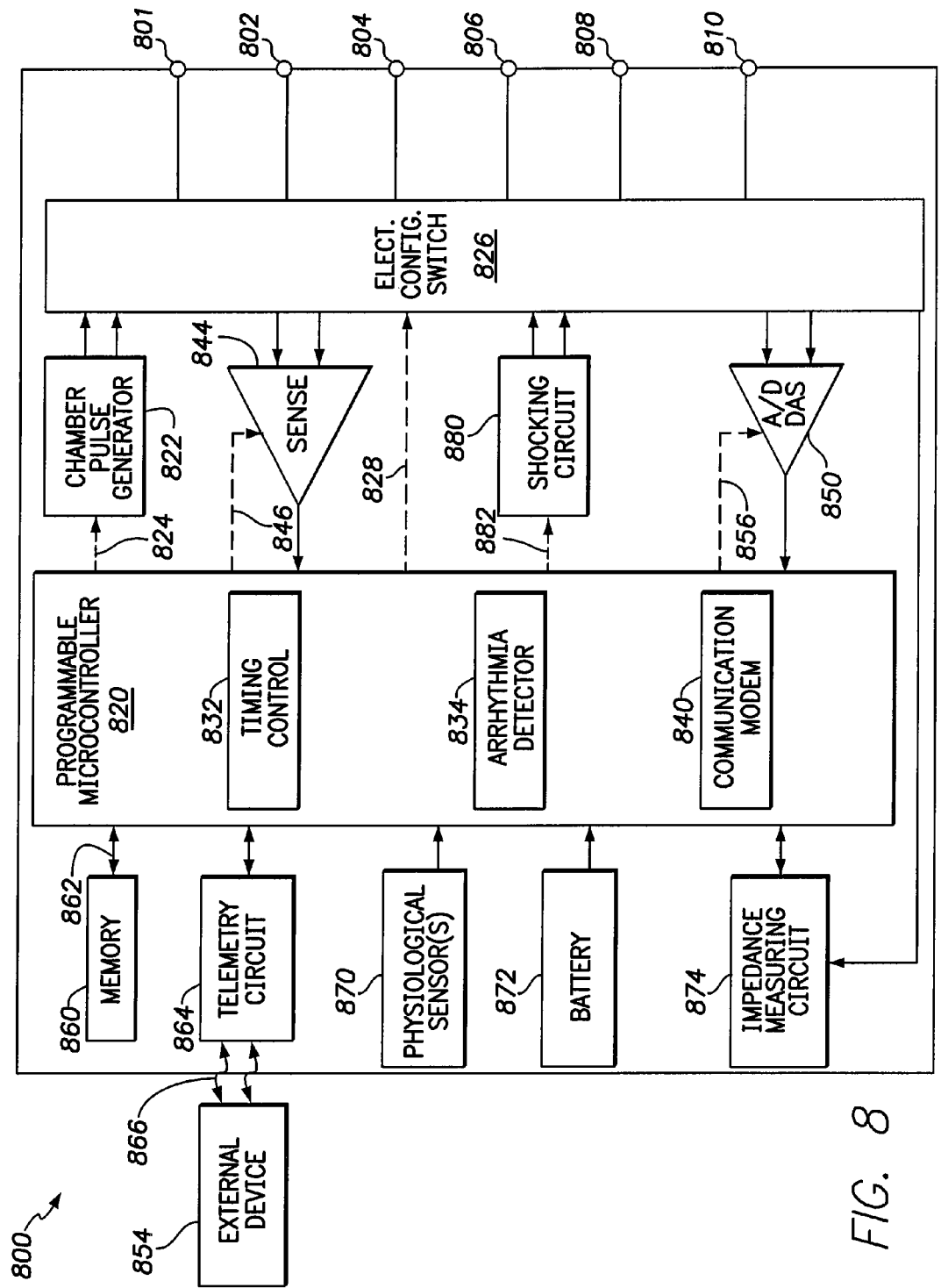
FIG. 8 illustrates an exemplary block diagram of the electrical components of an LIMD.

FIG. 8 shows an exemplary LIMD 800 configured for dual-chamber functionality from a primary location within a single chamber of the heart. For example, the LIMD 800 may be implemented as a pacemaker, equipped with both atrial and ventricular sensing and pacing circuitry. Alternatively, the LIMD 800 may be implemented with a reduced set of functions and components. For instance, the LIMD 800 may be implemented without ventricular sensing and pacing. The LIMD 800 may also be implemented with an increased set of functions. For example, if the LIMD 800 includes a coil type electrode, the LIMD may be configured to include cardioversion and/or shocking therapy capability.

The LIMD 800 has a housing 801 to hold the electronic/computing components. The housing 801 (which is often referred to as the "can", "case", "encasing", or "case electrode") may be programmably selected to act as the return electrode for certain stimulus modes. Electronics within the housing 801 includes a plurality of terminals 802, 804, 806, 808, 810 that interface with electrodes of the LIMD. For example, the terminals may include: a terminal 802 that connects with a first electrode associated with the housing (e.g. electrode 410) and located in a first chamber; a terminal 804 that connects with a second electrode associated with the housing (e.g., electrode 411) and also located in the first chamber; a terminal 806 that connects with a third electrode associated with the housing (e.g. electrode 412) and located in the first chamber and possibly partially extending into tissue associated with a second chamber; and two additional terminals 808, 810 that connect with one or more additional electrodes (e.g., electrode 524), if available. The type and location of each electrode may vary. For example, the electrodes may include various combinations of ring, tip, coil and shocking electrodes and the like.

The LIMD 800 includes a programmable microcontroller 820 that controls various operations of the LIMD 800, including cardiac monitoring and stimulation therapy. Microcontroller 820 includes a microprocessor (or equivalent control circuitry), RAM and/or ROM memory, logic and timing circuitry, state machine circuitry, and I/O circuitry.

LIMD 800 further includes a first chamber pulse generator 822 that generates stimulation pulses for delivery by one or more electrodes coupled thereto. The pulse generator 822 is controlled by the microcontroller 820 via control signal 824. The pulse generator 822 is coupled to the select electrode(s) via an electrode configuration switch 826, which includes multiple switches for connecting the desired electrodes to the appropriate I/O circuits, thereby facilitating electrode programmability. The switch 826 is controlled by a control signal 828 from the microcontroller 820.

In the example of FIG. 8, a single pulse generator 822 is illustrated. Optionally, the LIMD 800 may include multiple pulse generators, similar to pulse generator 822, where each pulse generator is coupled to one or more electrodes and controlled by the microcontroller 820 to deliver select stimulus pulse(s) to the corresponding one or more electrodes.

Microcontroller 820 is illustrated as including timing control circuitry 832 to control the timing of the stimulation pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The LIMD 800 includes sensing circuitry 844 selectively coupled to one or more electrodes through the switch 826. The sensing circuitry detects the presence of cardiac activity in the right chambers of the heart. The sensing circuitry 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 802 to sense low amplitude signal characteristics of atrial fibrillation. Switch 826 determines the sensing polarity of the cardiac signal by selectively closing the appropriate switches. In this way, the clinician may program the sensing polarity independent of the stimulation polarity.

The output of the sensing circuitry 844 is connected to the microcontroller 820 which, in turn, triggers or inhibits the pulse generator 822 in response to the absence or presence of cardiac activity. The sensing circuitry 844 receives a control signal 846 from the microcontroller 820 for purposes of controlling the gain, threshold, polarization charge removal circuitry (not shown), and the timing of any blocking circuitry (not shown) coupled to the inputs of the sensing circuitry.

In the example of FIG. 8, a single sensing circuit 844 is illustrated. Optionally, the LIMD 800 may include multiple sensing circuit, similar to sensing circuit 844, where each sensing circuit is coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The LIMD 800 further includes an analog-to-digital (A/D) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the LIMD 800 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 808 within each respective tier of therapy.

The operating parameters of the LIMD 800 may be non-invasively programmed into the memory 860 through a telemetry circuit 864 in telemetric communication via communication link 866 with the external device 854. The telemetry circuit 864 allows intracardiac electrograms and status information relating to the operation of the LIMD 800 (as contained in the microcontroller 820 or memory 860) to be sent to the external device 854 through the established communication link 866.

The IMD 802 can further include magnet detection circuitry (not shown), coupled to the microcontroller 820, to detect when a magnet is placed over the unit. A magnet may be used by a clinician to perform various test functions of the unit 802 and/or to signal the microcontroller 820 that the external programmer 854 is in place to receive or transmit data to the microcontroller 820 through the telemetry circuits 864.

The LIMD 800 may be equipped with a communication modem (modulator/demodulator) 840 to enable wireless communication with a remote device, such as a second implanted LIMD in a master/slave arrangement, such as described in U.S. Pat. No. 7,630,767. In one implementation, the communication modem 840 uses high frequency modulation. As one example, the modem 840 transmits signals between a pair of LIMD electrodes, such as between the can 800 and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller as a standalone component.

The LIMD 800 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and ventricular pacing pulses are administered. While shown as being included within the unit 802, the physiologic sensor(s) 870 may be external to the unit 802, yet still be implanted within or carried by the patient. Examples of physiologic sensors might include sensors that, for example, sense respiration rate, pH of blood, ventricular gradient, activity, position/posture, temperature, minute ventilation (MV), and so forth.

A battery 872 provides operating power to all of the components in the LIMD 800. The battery 872 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 872 also desirably has a predictable discharge characteristic so that elective replacement time can be detected. As one example, the unit 802 employs lithium/silver vanadium oxide batteries.

The LIMD 800 further includes an impedance measuring circuit 874, which can be used for many things, including: impedance surveillance during the acute and chronic phases for proper LIMD positioning or dislodgement; detecting operable electrodes and automatically switching to an operable pair if dislodgement occurs; measuring respiration or minute ventilation; measuring thoracic impedance; detecting when the device has been implanted; measuring stroke volume; and detecting the opening of heart valves; and so forth. The impedance measuring circuit 874 is coupled to the switch 826 so that any desired electrode may be used.

The microcontroller 820 further controls a shocking circuit 880 by way of a control signal 882. The shocking circuit 880 generates shocking pulses of low (e.g., up to 0.5 joules), moderate (e.g., 0.5-10 joules), or high energy (e.g., 811 to 40 joules), as controlled by the microcontroller 820. Such shocking pulses are applied to the patient's heart 808 through shocking electrodes, if available on the LIMD. It is noted that the shock therapy circuitry is optional and may not be implemented in the LIMD, as the various LIMDs described above and further below will typically not be configured to deliver high voltage shock pulses. On the other hand, it should be recognized that an LIMD may be used within a system that includes backup shock capabilities, and hence such shock therapy circuitry may be included in the LIMD.

Figure 9:
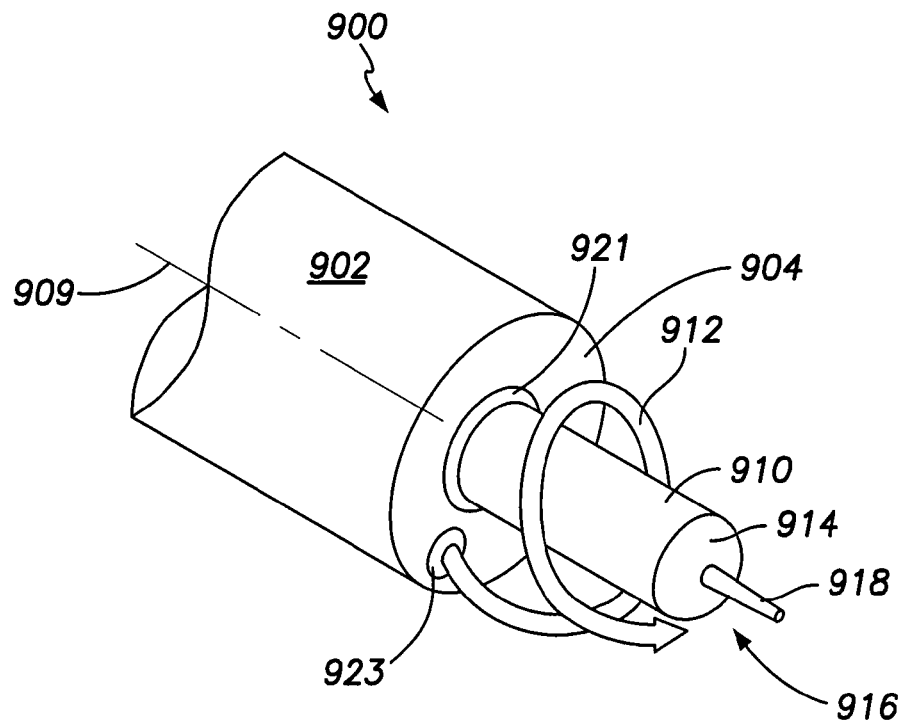
FIG. 9 illustrates a bottom plan view of a LIMD formed in accordance with an alternative embodiment.

FIG. 9 illustrates a bottom plan view of an LIMD 900 formed in accordance with an alternative embodiment. The LIMD 900 comprises a proximal base 904, a distal top end (not shown), and a housing 902 extending between the proximal base 904 and the distal top end. The housing 902 is elongated and tubular in shape and extends along a longitudinal axis 909.

The base 904 includes inner and outer electrodes 910, 912 securely affixed at base mounts 921, 923 to the base 904. The inner and outer electrodes 910, 912 projected outward from the base 904. For example, the outer electrode 912 is formed as a large semi-circular spike or large gauge wire that wrap about the inner electrode 910. The inner and outer electrodes 910, 912 are physically and electrically separated from one another. The outer electrode 912 is positioned near the periphery of the base 904 and may expose a large portion of the conductive surface area thereof. The outer electrode 912 may be configured to operate as an anode during sensing and/or during delivery of a stimulus pulse. The inner electrode 910 may extend outward along the longitudinal axis 909 and be shaped as a straight pin. The electrode 910 may have an active electrode area 914 located at the distal end 916 thereof. Optionally, a pin or needle 918 may extend beyond the active electrode area 914 to serve as a locating device. The electrode 910 may be configured to operate as a cathode during sensing and/or during delivery of a stimulus pulse. Optionally, needle 918 may be the active electrode area and area 914 may be insulated. Optionally, the inner electrode 912 may have a common diameter along the length thereof with a pointed needle tip.

The inner and outer electrodes 910, 912 may be formed as a single conductive wires or bundles of conductive wires, where none or a desired portion of the wire is covered with insulation, while a desired portion is exposed. By covering a portion of the electrodes 910, 912 with insulation, this limits electrical conduction of the conductive wire to tissue surrounding the desired portion. Optionally, the outer electrode 912 may be entirely covered in insulation or otherwise formed to be inoperative as an electrode. Instead, a helical active fixation member may be provided with a similar shape as, and in the place of, the outer electrode 912.

Figure 10:
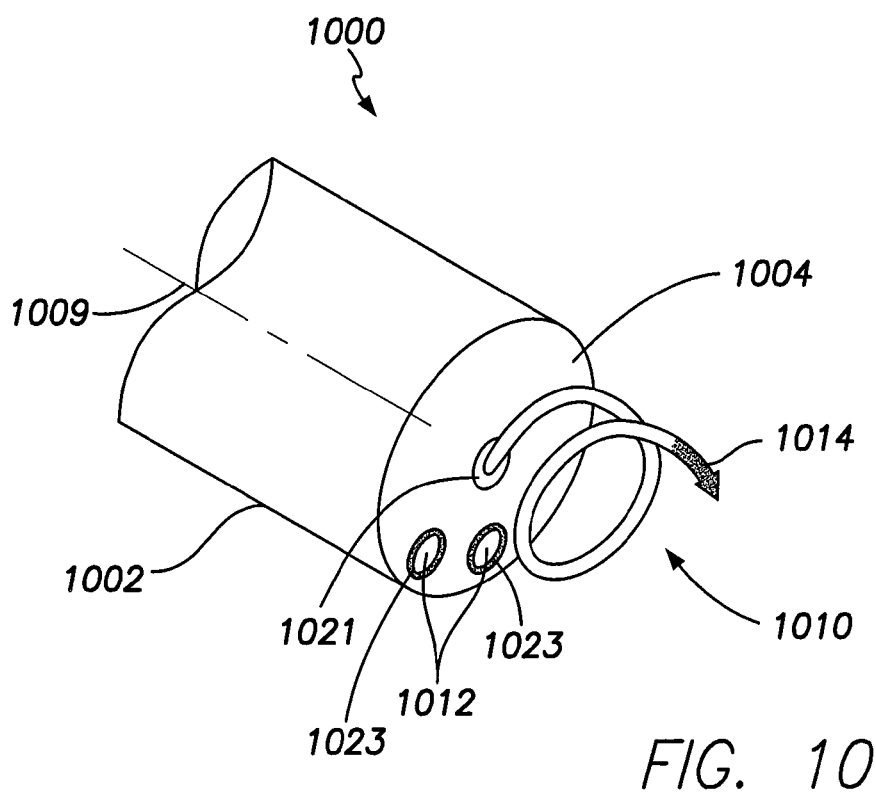
FIG. 10 illustrates a bottom plan view of a LIMD formed in accordance with an alternative embodiment.

FIG. 10 illustrates a bottom plan view of an LIMD 1000 formed in accordance with an alternative embodiment. The LIMD 1000 comprises a proximal base 1004, a distal top end (not shown), and a housing 1002 extending between the proximal base 1004 and the distal top end. The base 1004 includes inner and outer electrodes 1010, 1012 securely affixed at base mounts 1021, 1023 to the base 1004. The inner and outer electrodes 1010, 1012 project outward from the base 1004. For example, the outer electrodes 1012 may be formed as raised bump or surface electrodes that do not active affix to tissue. The inner and outer electrodes 1010, 1012 are physically and electrically separated from one another. The outer electrodes 1012 are positioned near the periphery of the base 1004. The outer electrodes 1012 may be configured to operate one as an anode and one as a cathode during sensing and/or during delivery of a stimulus pulse. The inner electrode 1010 may extend outward along the longitudinal axis 1009 and be shaped as a helix or straight pin. The electrode 1010 may have an active electrode area 1014 located at the distal end. The surface or bump type electrodes 1012 may be coupled to the conductive network of the local chamber (e.g. when positioned proximate the SA node or triangle of Koch and away from the ventricular vestibule). The electrode 1010 may be coupled to the conductive network of the adjacent chamber (e.g. when positioned proximate to the ventricular vestibule). Optionally, the base mounts 921, 923, 1021, 1023 may be formed with cavities in the bases 904, 1004 and to surround the corresponding electrodes 910, 912, 1010, 1012. The cavities may represent circular indented pockets that receive a steroid or other biological agent that facilitates a desired behavior at the tissue wall that engages the electrodes 910, 912, 1010, 1012. For example, the steroid may encourage healing and discourage rejection of the electrode. As another example, the steroid may encourage the wall tissue to grow to the electrode and base. As another option, the steroid may reduce scarring when the wall tissue engages the electrode.

Figure 11A:
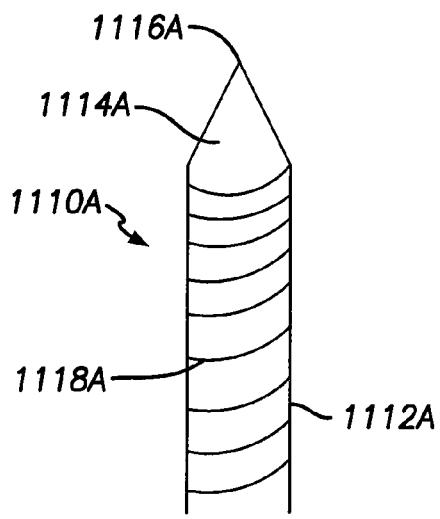
FIGS. 11A-11C illustrate alternative electrode configurations that may be used alone or in combination.
Figure 11B:
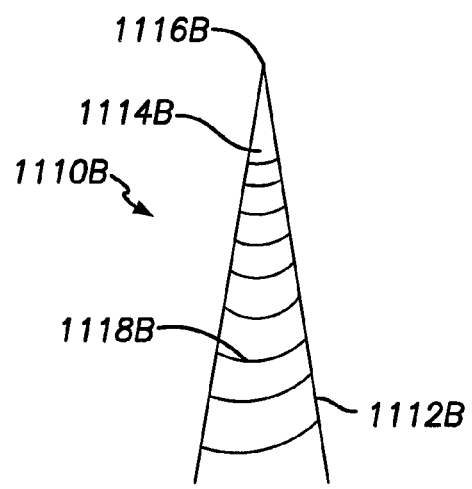
Figure 11C:
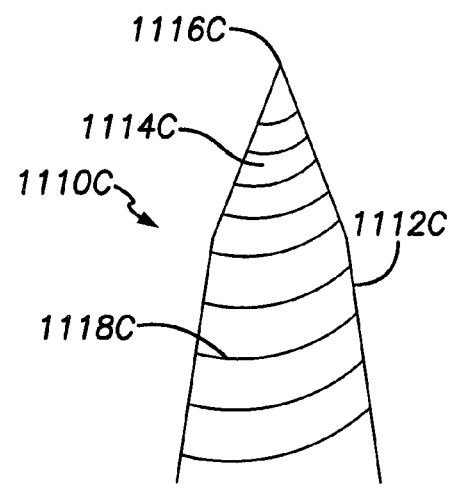

FIGS. 11A-11C illustrate alternative electrode configurations that may be used alone or in combination. FIGS. 11A-11C illustrate electrodes 1110A-1110C having insulated proximal segments 1112A-1112C and distal active electrode areas 1114A-1114C. The proximal segment 1112A in FIG. 11A has a common relatively small diameter throughout, while the active electrode area 1114A is tapered to a distal end 1116A. In FIG. 11B, the proximal segment 1112B and active electrode area 1114B are tapered at a common angle to a point at distal end 1116B. In FIG. 11C, the proximal segment 1112C and active electrode area 1114C are both tapered but at different angles. Optionally, the electrode may be a straight pin with no taper at the point or elsewhere. Optionally, the exterior of the proximal segment 1114A-1114C may have a threaded contour 1118A-1118C, such as on a screw or bolt.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determine with reference to the appended claims, along with the full scope of equivalents to which such claims are entitled. In the appended claims, the terms "including" and "in which" are used as the plain-english equivalents of the respective terms "comprising" and "wherein". Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A leadless intra-cardiac medical device (LIMD), comprising:

a housing configured to be implanted entirely within a single local chamber of the heart, the local chamber having local wall tissue that constitutes part of a conduction network of the local chamber;

the housing including a stabilizer arm having a distal end that extends outward from the housing, the stabilizer arm having a pusher cup located at the distal end, the pusher cup configure to receive a pusher tool, the stabilizer arm having a core structure that is torque and compression resistant such that when the pusher tool is rotated or moved longitudinally, the stabilizer arm conveys rotation and longitudinal force from the pusher tool to the housing;

a base on the housing, the base configured to be secured to tissue of interest that separates the local chamber from an adjacent chamber, the adjacent chamber having distal wall tissue, with respect to the local chamber, that constitutes part of a conduction network of the adjacent chamber;

a first electrode provided on the base and extending outward such that, when the device is implanted in the local chamber, the first electrode is configured to engage wall tissue at a distal activation site within the conduction network of the adjacent chamber;

an extension arm provided on the housing and extending outward from the housing;

a second electrode provided on the extension arm and located such that, when the extension arm is positioned in the local chamber, the second electrode is configured to engage wall tissue at a local activation site within the conduction network of the local chamber; and a controller within the housing to cause stimulus pulses to be delivered, in a synchronous manner, through the first and second electrodes to the distal and local activation sites, respectively, such that stimulus pulses delivered at the distal activation site are timed to cause contraction of the adjacent chamber in a predetermined relation to contraction of the local chamber.

2. The device of claim 1, wherein the stabilizer arm is joined to a top end of the housing, the extension arm having the second electrode located on a distal end thereof to extend into and engage the local wall tissue in an appendage area of the local chamber, the stabilizer arm having a distal end that extends to and engages an opposed stabilization area of the local chamber.

3. The device of claim 1, wherein the tissue of interest represents a portion of the triangle of Koch, the second electrode is configured to engage the distal activation site which is in the ventricular vestibule, the first electrode is configured to engage the local activation site which is in the triangle of Koch, the first and second electrodes delivering stimulus pulses to the triangle of Koch and the ventricular vestibule to initiate activation in a right atrium and right ventricle, respectively.

4. The device of claim 1, wherein the controller is configured to control delivery, from the first and second electrodes, of the stimulus pulses to a right atrium and a right ventricle, while the housing is entirely located in one of the right atrium and right ventricle.

5. The device of claim 1, wherein at least one of the first and second electrodes represent surface bump type electrodes that passively engage the wall tissue.

6. The device of claim 1, wherein the base includes mounting elements to secure the first and second electrodes to the housing in an electrically isolated manner.

7. The device of claim 1, wherein the second electrode has different first and second cross-sections at proximal and distal ends thereof.

8. The device of claim 1, wherein the second electrode includes a conductive wire that has different first and second iso-diameters at the proximal and distal ends thereof.

9. The device of claim 1, wherein the base includes spikes to facilitate active fixation to the septum.

10. A leadless intra-cardiac medical device (LIMD), comprising:

a housing configured to be implanted entirely within a single local chamber of the heart, the local chamber having local wall tissue that constitutes part of a conduction network of the local chamber;

a base on the housing, the base configured to be secured to tissue of interest that separates the local chamber from an adjacent chamber, the adjacent chamber having distal wall tissue, with respect to the local chamber, that constitutes part of a conduction network of the adjacent chamber;

a first electrode provided on the base and extending outward such that, when the device is implanted in the local chamber, the first electrode is configured to engage wall tissue at a distal activation site within the conduction network of the adjacent chamber;

an extension arm provided on the housing and extending outward from the housing;

the housing including a stabilizer arm, the extension arm and stabilizer arm pivotally joined to a hinge assembly located at a top end of the housing;

a second electrode provided on the extension arm and located such that, when the extension arm is positioned in the local chamber, the second electrode is configured to engage wall tissue at a local activation site within the conduction network of the local chamber; and a controller within the housing to cause stimulus pulses to be delivered, in a synchronous manner, through the first and second electrodes to the distal and local activation sites, respectively, such that stimulus pulses delivered at the distal activation site are timed to cause contraction of the adjacent chamber in a predetermined relation to contraction of the local chamber.

11. The device of claim 10, wherein the tissue of interest represents a portion of the triangle of Koch, the second electrode is configured to engage the distal activation site which is in the ventricular vestibule, the first electrode is configured to engage the local activation site which is in the triangle of Koch, the first and second electrodes delivering stimulus pulses to the triangle of Koch and the ventricular vestibule to initiate activation in a right atrium and right ventricle, respectively.

12. The device of claim 10, wherein the controller is configured to control delivery, from the first and second electrodes, of the stimulus pulses to a right atrium and a right ventricle, while the housing is entirely located in one of the right atrium and right ventricle.

13. The device of claim 10, wherein at least one of the first and second electrodes represent surface bump type electrodes that passively engage the wall tissue.

14. The device of claim 10, wherein the base includes mounting elements to secure the first and second electrodes to the housing in an electrically isolated manner.

15. The device of claim 10, wherein the second electrode has different first and second cross-sections at proximal and distal ends thereof.

16. The device of claim 10, wherein the second electrode includes a conductive wire that has different first and second iso-diameters at the proximal and distal ends thereof.

17. The device of claim 10, wherein the base includes spikes to facilitate active fixation to the septum.

18. A leadless intra-cardiac medical device (LIMD), comprising:

a housing configured to be implanted entirely within a single local chamber of the heart, the local chamber having local wall tissue that constitutes part of a conduction network of the local chamber;

a base on the housing, the base configured to be secured to tissue of interest that separates the local chamber from an adjacent chamber, the adjacent chamber having distal wall tissue, with respect to the local chamber, that constitutes part of a conduction network of the adjacent chamber;

a first electrode provided on the base and extending outward such that, when the device is implanted in the local chamber, the first electrode is configured to engage wall tissue at a distal activation site within the conduction network of the adjacent chamber;

an extension arm provided on the housing and extending outward from the housing;

the housing including a stabilizer arm, the extension arm and stabilizer arm securely joined to a top end of the housing, the extension arm and stabilizer arm being biased to flare outward away from one another when in a deployed position such that distal ends of the stabilization and extension arms engage the local chamber in opposed areas remote from the base of the housing;

a second electrode provided on the extension arm and located such that, when the extension arm is positioned in the local chamber, the second electrode is configured to engage wall tissue at a local activation site within the conduction network of the local chamber; and a controller within the housing to cause stimulus pulses to be delivered, in a synchronous manner, through the first and second electrodes to the distal and local activation sites, respectively, such that stimulus pulses delivered at the distal activation site are timed to cause contraction of the adjacent chamber in a predetermined relation to contraction of the local chamber.

19. The device of claim 18, wherein the tissue of interest represents a portion of the triangle of Koch, the second electrode is configured to engage the distal activation site which is in the ventricular vestibule, the first electrode is configured to engage the local activation site which is in the triangle of Koch, the first and second electrodes delivering stimulus pulses to the triangle of Koch and the ventricular vestibule to initiate activation in a right atrium and right ventricle, respectively.

20. The device of claim 18, wherein the controller is configured to control delivery, from the first and second electrodes, of the stimulus pulses to a right atrium and a right ventricle, while the housing is entirely located in one of the right atrium and right ventricle.

21. The device of claim 18, wherein at least one of the first and second electrodes represent surface bump type electrodes that passively engage the wall tissue.

22. The device of claim 18, wherein the base includes mounting elements to secure the first and second electrodes to the housing in an electrically isolated manner.

23. The device of claim 18, wherein the second electrode has different first and second cross-sections at proximal and distal ends thereof.

24. The device of claim 18, wherein the second electrode includes a conductive wire that has different first and second iso-diameters at the proximal and distal ends thereof.

25. The device of claim 18, wherein the base includes spikes to facilitate active fixation to the septum.

26. A leadless intra-cardiac medical device (LIMD), comprising:

a housing configured to be implanted entirely within a single local chamber of the heart, the local chamber having local wall tissue that constitutes part of a conduction network of the local chamber;

a base on the housing, the base configured to be secured to tissue of interest that separates the local chamber from an adjacent chamber, the adjacent chamber having distal wall tissue, with respect to the local chamber, that constitutes part of a conduction network of the adjacent chamber;

a first electrode provided on the base and extending outward such that, when the device is implanted in the local chamber, the first electrode is configured to engage wall tissue at a distal activation site within the conduction network of the adjacent chamber;

an extension arm provided on the housing and extending outward from the housing;

the housing being elongated along a longitudinal axis, the housing being joined to the extension arm such that the extension arm moves between an introduction contracted position substantially in-line with the longitudinal axis of the housing and a deployed flared position that projects at an acute angle from the longitudinal axis of the housing to position the first electrode against the local wall tissue;

a second electrode provided on the extension arm and located such that, when the extension arm is positioned in the local chamber, the second electrode is configured to engage wall tissue at a local activation site within the conduction network of the local chamber; and a controller within the housing to cause stimulus pulses to be delivered, in a synchronous manner, through the first and second electrodes to the distal and local activation sites, respectively, such that stimulus pulses delivered at the distal activation site are timed to cause contraction of the adjacent chamber in a predetermined relation to contraction of the local chamber.

27. The device of claim 26, wherein the tissue of interest represents a portion of the triangle of Koch, the second electrode is configured to engage the distal activation site which is in the ventricular vestibule, the first electrode is configured to engage the local activation site which is in the triangle of Koch, the first and second electrodes delivering stimulus pulses to the triangle of Koch and the ventricular vestibule to initiate activation in a right atrium and right ventricle, respectively.

28. The device of claim 26, wherein the controller is configured to control delivery, from the first and second electrodes, of the stimulus pulses to a right atrium and a right ventricle, while the housing is entirely located in one of the right atrium and right ventricle.

29. The device of claim 26, wherein at least one of the first and second electrodes represent surface bump type electrodes that passively engage the wall tissue.

30. The device of claim 26, wherein the base includes mounting elements to secure the first and second electrodes to the housing in an electrically isolated manner.

31. The device of claim 26, wherein the second electrode has different first and second cross-sections at proximal and distal ends thereof.

32. The device of claim 26, wherein the base includes spikes to facilitate active fixation to the septum.

* * * * *